US005641800A

United States Patent [19]
Bach et al.

[11] Patent Number: 5,641,800
[45] Date of Patent: Jun. 24, 1997

[54] 1H-INDOLE-1-FUNCTIONAL SPLA$_2$ INHIBITORS

[75] Inventors: Nicholas J. Bach, Indianapolis; Robert D. Dillard, Zionsville; Susan E. Draheim, Indianopolis, all of Ind.

[73] Assignee: Eli Lilly and Company, Indianapolis, Ind.

[21] Appl. No.: 421,097

[22] Filed: Apr. 13, 1995

Related U.S. Application Data

[62] Division of Ser. No. 278,353, Jul. 21, 1994, abandoned.

[51] Int. Cl.$^6$ .................... C07D 209/08; C07F 9/553; A61K 31/40
[52] U.S. Cl. .................... 514/415; 514/91; 548/113; 548/481
[58] Field of Search .................... 548/500, 113, 548/481; 514/415, 91

[56] References Cited

U.S. PATENT DOCUMENTS

| | | | |
|---|---|---|---|
| 2,825,734 | 3/1958 | Speeter | 260/319 |
| 3,242,163 | 3/1966 | Sarett et al. | 260/211 |
| 3,259,622 | 7/1966 | Shen et al. | 260/247.5 |
| 3,271,416 | 9/1966 | Shen et al. | 260/319 |
| 3,351,630 | 11/1967 | Shen | 260/326.12 |
| 3,449,363 | 6/1969 | Littel | 260/326.13 |
| 3,624,103 | 11/1971 | DeMartilis et al. | 260/326.13 A |
| 4,012,513 | 3/1977 | Birchall et al. | 424/251 |
| 4,397,850 | 8/1983 | Nadelson et al. | |
| 5,132,319 | 7/1992 | Girard | 514/415 |

FOREIGN PATENT DOCUMENTS

| | | |
|---|---|---|
| 490263A | 6/1992 | European Pat. Off. . |
| 620214A | 10/1994 | European Pat. Off. . |
| 620 215A | 10/1994 | European Pat. Off. . |
| WO88/06885 | 9/1988 | WIPO . |
| WO92/06088 | 4/1992 | WIPO . |

OTHER PUBLICATIONS

*Chemical Abstracts*, vol. 83, 1975 131402U, "Nonarcotic analgetic and antinflammatory agents". 1–Carboxyalklyl–3–acylindoies.

Kreft, A.; Nelson, Jr. et al; "Structure–activity relationships leading to WAY–121, 520, a tris aryl type, indomethacin–based phospholipase A2 (PLA2)/leukotriene biosynthesis inhibitor", Issue vol. 39 (1993), pp. C33–C35, ISSN 0065–4299; publ. by Birkhauser Verlag, Basel Switzerland; (Proceedings of the Sixth International Research Assoc., Sep. 20–24, 1992 at White Haven, PA/USA, Ed., D.W. Morgan and A.K. Welton.

Seilhamer, Jeffery, et al., "Cloning and Recombinant Expression of Phospholipase A$_2$ present in Rheumatoid Arthritic Synovial Fluid"; *The Journal of Biological Chemistry*, 254:10, Apr. 5, 1989, pp. 5335–5338.

Kramer, Ruth et al., "Structure and Properties of a Human Non–Pancreatic Phospholipase A$_2$", *The Journal of Biological Chemistry*, 264.10, Apr. 5, 1989, pp. 5768–5775.

Reynolds et al., "Analysis of Human Synovial Fluid Phospholipase A2 on Short Chain Phosphatidylcholine–Mixed Micelles; Development of a Spectrophotometric Assay Suitable for a Microtiterplate Reader", Analytical Biochem, 204, pp. 190–197, 1992.

Rossum, et al., "Cumulative Dose–Response Curves II, Technique for the making of dose response curves in isolated organs and the evaluation of drug parameters", Arch. Int. Pharmacodyn, 143, No. 3–4, pp. 299–330, 1963.

Waud, Douglas R. "Analysis of Dose–Response Relationships", Dept. of Pharma, Univ. of Mass. Med. Center, 145–179 (no date available).

Alemany, A; Alvarex, E.; Lopez, O. and Herraez, M.E.; No. 565—"Inhibiteurs d'enzymes. XII—Preparation de (propargyamino–2–ethyl)–3 indoles"; *Bulletin Do La Societe 'Chimiqque DeFrance*, 1974, No. 12, pp. 2883–2888.

Kollenz, Gert; Labes, Christa, "Indol–Umlagerung von 1–Diphenyl amino–2,3–dihydro–2,3–pyrrolidionen"; *Liebigs Ann. Chem.*, 1975, pp. 1979–1983.

Kreft, A.; Nelson, Jr., et al; "Structure–activity relationships leadigng to WAY–121,520, a tris aryl type, Nidomethacin–based, phospholipase A2 (PLA2)/leukotriene biosynthesis inhibitor", Issue vol. 39 (1993), pp. C33–C35, ISSN 0065–4299; publ. by Birkhauser Verlag, Basel Switzerland; (Proceeding of the Sixth International Research Assoc., Sep. 20–24, 1992 at White Haven, PA/USA, Ed., D.W. Morgan and A.K. Welton.

Walton, E., et al., "Some Analogs of 1–p–Chlorobenzyl–5–methylindole–3–acetic Acid", *J. Med. Chem.*, vol. 11, 1968, pp. 1252–1255.

Andreani, A. et al., "Nonsteroidal Antiinflammatory Agents. 2. Synthesis and Biological Activity of 2–Chlorindolecarboxylic Acids"; *Journal of Medicinal Chemistry*, vol. 20, No. 10, 1977, pp. 1344–1346.

Julia, Marc, et al., "No. 208–Recherches en serie indolique. XIII. Sur quelques methoxy–5 et. –6 tryptamines", *Bulletin de La Societe Chimique de France*, Paris, France; 1965, pp. 1411–1417.

Chemical Abstracts, vol. 1/2. No. 24, Abstract No. 223181s; "Kinetis of hydrolysis of indomethacin and indomethacin ester predrugs in aqueous solution", Jun. 11, 1990, p. 407.

Chemical Abstracts Service, "Registry Handbook", Number Section, Registry Numbers (see, CAS RN 6264–33–1) 1965–1971, Publ. American Chemical Society.

Von K. H. Boltze; O. Brendler, et al., "Chemische Struktur und antiphlogistische Wirkung in der Reihe der substituierten Indol–3–essigsauren", Arznermittel Forschung Drug Research, vol. 30 (II), No. 8A, 1980, Aulendorf, DE, pp. 1314–1325.

*Primary Examiner*—David B. Springer
*Attorney, Agent, or Firm*—Roger S. Benjamin; David E. Boone

[57] ABSTRACT

A class of novel 1H-indole-1-functional compounds is disclosed together with the use of such indole compounds for inhibiting sPLA$_2$ mediated release of fatty acids for treatment of conditions such as septic shock. The compounds are 1H-indole-1-acetamides, 1H-indole-1-acetic acid hydrazides, and 1H-indole-1-glyoxylamides.

21 Claims, No Drawings

1H-INDOLE-1-FUNCTIONAL SPLA$_2$ INHIBITORS

This application is a division of application Ser. No. 08/278,353, filed Jul. 21, 1994 abandoned.

BACKGROUND OF THE INVENTION

1. Field of the Invention

This invention relates to novel 1H-indole-1-glyoxylamides, 1H-indole-1-acetamides, and 1H-indole-1-hydrazides useful for inhibiting sPLA$_2$ mediated release of fatty acids for conditions such as septic shock.

2. Background Information

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, issue of Apr. 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$; such as septic shock, adult respiratory distress syndrome, pancreatitis, trauma, bronchial asthma, allergic rhinitis, rheumatoid arthritis, and etc.

The article, "No. 565. -Inhibiteurs d'enzymes. XII. Preparation de (propargyamino-2 ethyl)-3 indoles" by A. Alemanhy, E. Fernandez Alvarez, O. Nieto Lopey and M. E. Rubio Herraez; *Bulletin DO La Societe Chimiqque De France*, 1974, No. 12, pgs. 2883–2888 describes various indolyl-3 glyoxamides which are hydrogen substituted on the 6 membered ring of the indole nucleus.

The article "Indol-Umlagerung von 1-Diphenylamino-2, 3-dihydro-2,3-pyrroldionen" by Gert Kollenz and Christa Labes; Liebigs Ann. Chem., 1975, pgs. 1979–1983 describes phenyl substituted 3-glyoxylamides.

The abstract, "Nonnarcotic analgesic and antiinflammatory agents. 1-Carboxyalkyl-3-acylindoles" by Allais, Andre., et. al., Chemical Abstracts No. 131402u, Vol. 83, 1975 depicts indole formula with a —CH$_2$CO$_2$H group on the indole nitrogen.

The article, "Structure-activity relationships leading to WAY-121, 520, a tris aryl-type, indomethacin-based, phospholipase A$_2$ (PLA$_2$)/leukotriene biosynthesis inhibitor", by A Kreft, et. al., *Agents and Actions, Social Conference Issue* Vol. 39 (1993),pp. C33–C35, ISSN 0065-4299, published by Birkhauser Verlag, Basel Switzerland; (Proceedings of the Sixth International Conference of the Inflammation Research Association, Sep. 20–24, 1992, at White Haven, PA/USA, Guest Editors, D. W. Morgan and A. K. Welton) describes the inhibition of phospholipase A2 by indomethacin analogs. Indole compounds having benzyl and acidic substituents are described.

The article, "Some Analogs of 1-p-chlorobenzyl-5-methylindole-3-acetic acid" by E. Walton, et. al., *J. Med. Chem.*, Vol. 11, 1968, pp. 1252–1255, describes the preparation of isomeric methyl 3-1-(1-p-chlorobenzyl-5-methoxy-3-methyl indole-2) propionate.

European Patent 490263 discloses oxoacetamide derivatives of indoles having serotonin receptor activity.

U.S. Pat. No. 1,825,734 describes the preparation of 3-(2-amino-1-hydroxyethyl) indoles using 3-indole glyoxylamide intermediates such as 1-phenethyl-2-ethyl-6-carboxy-N-propyl-3-indoleglyoxylamide (see, Example 30).

U.S. Pat. No. 2,890,233 describes several amide derivatives of 3-indoleacetic acids.

U.S. Pat. No. 3,271,416 describes indolyl aliphatic acids as sun screening agents and intermediates. These acids may be —NH$_2$ substituted.

U.S. Pat. No. 3,351,630 describes alpha-substituted 3-indolyl acetic acid compounds and their preparation inclusive of glyoxylamide intermediates.

U.S. Pat. No. 3,449,363 describes trifluoromethylindoles having glyoxylamide groups at the 3 position of the indole nucleus. These compounds are stated to be analgesics in antagonizing phenyl-p-quinone "writhing syndrome."

World Patent application WO 9206088 describes indole compounds useful for treatment of circulatory diseases, chromosis and renal diseases.

Chemical Abstracts Vol. 83, 1975 131402u, "Nonarcotic analgetic and antiinflammatory agents. 1-Carboxyalkyl-3-acylindoles", describes various analgesic and antiinflammatory indolencetic acids.

U.S. Pat. No. 4,397,850 prepares isoxazolyl indolamines using glyoxylamide indoles as intermediates.

U.S. Pat. No. 5,132,319 describes certain 1-(hydroxylaminoalkyl) indoles derivatives as inhibitors of leukotriene biosynthesis.

It is desirable to develop new compounds and treatments for sPLA$_2$ induced diseases.

SUMMARY OF THE INVENTION

This invention is a novel use of compounds known as 1H-indole-1-functional compounds wherein the functionality at the 1-position (viz., the indole nitrogen) is selected from the group consisting of acetamide, acetic acid hydrazide and glyoxylamide as depicted in the general formula (G) below:

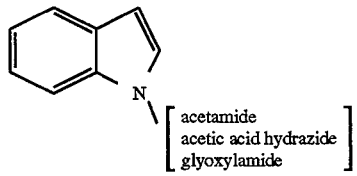

These 1H-indole-1-functional compounds are effective in inhibiting human sPLA$_2$ mediated release of fatty acids.

This invention is also a novel class of 1H-indole-1-acetamides having potent and selective effectiveness as inhibitors of human sPLA$_2$.

This invention is also a novel class of 1H-indole-1-acetic acid hydrazides (hereinafter called, "hydrazides") having potent and selective effectiveness as inhibitors of human sPLA$_2$.

This invention is also a novel class of 1H-indole-1-glyoxylamides having potent and selective effectiveness as inhibitors of human sPLA$_2$.

This invention is also a pharmaceutical composition containing a 1H-indole-1-functional compound selected from the group consisting of the novel 1H-indole-1-acetamides, 1H-indole-1-hydrazides, and 1H-indole-1-glyoxylamides of the invention and mixtures thereof.

This invention is also a method of preventing and treating septic shock, adult respiratory distress syndrome, pancreatitis, trauma, bronchial asthma, allergic rhinitis, rheumatoid arthritis, and related diseases by contact with a therapeutically effective amount of the 1H-indole-1-functional aceramides, hydrazides and glyoxylamides of the invention, or mixtures thereof.

DETAILED DESCRIPTION OF THE INVENTION

Definitions:

The 1H-indole-1-acetamides, hydrazides, and glyoxylamides of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridinyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

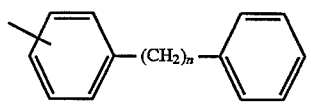
(bb)

where n is a number from 1 to 8.

The term, "non-interfering substituent", refers to radicals suitable for substitution at positions 4, 5, 6, and/or 7 on the indole nucleus (as hereinafter depicted in Formula I) and radical(s) suitable for substitution on the heterocyclic radical and carbocyclic radical as defined above. Illustrative non-interfering radicals are $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —$(CH_2)_n$—$CO_2$H, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

The term, "acidic group" means an organic group which when attached to an indole nucleus, through suitable linking atoms (hereinafter defined as the "acid linker"), acts as a proton donor capable of hydrogen bonding. Illustrative of an acidic group are the following:

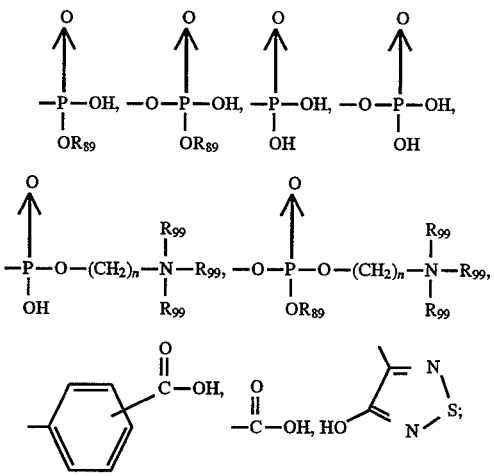

where n is 1 to 8, $R_{89}$ is a metal or $C_1$–$C_{10}$ alkyl, and $R_{99}$ is hydrogen or $C_1$–$C_{10}$ alkyl.

The words, "acid linker" refer to a divalent linking group symbolized as, —($L_a$)—, which has the function of joining the 6 or 7 position of the indole nucleus to an acidic group in the general relationship:

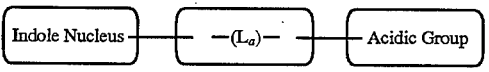

The words, "acid linker length", refer to the number of atoms (excluding hydrogen) in the shortest chain of the linking group —($L_a$)— that connects the 6 or 7 position of the indole nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative acid linker groups are;

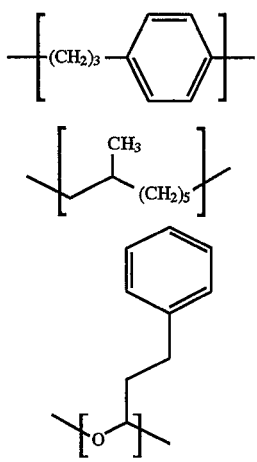

wherein, groups (a), (b), and (c) have acid linker lengths of 5, 7, and 2, respectively.

The term, "amine", includes primary, secondary and tertiary amines.

Types of 1H-Indole-1-Functional Compounds of the Invention:

There are three types of 1H-indole-1-functional compounds of the invention described as types (A), (B), and (C) below:

A) 1H-indole-1-acetamide compounds of the invention having the general formula (I);

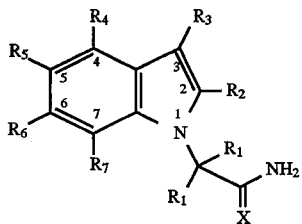

where each $R_1$ is independently hydrogen, or $C_1$–$C_3$ alkyl; X is selected from oxygen or sulfur; and all other groups are as hereinafter defined.

B) 1H-indole-1-hydrazide compounds of the invention having the general formula (II);

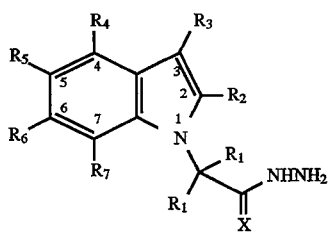

where each $R_1$ is independently, hydrogen, or $C_1$–$C_3$ alkyl; X is selected from oxygen or sulfur; and all other groups are as hereinafter defined.

C) 1H-indole-1-glyoxylamide compounds of the invention having the general formula (III);

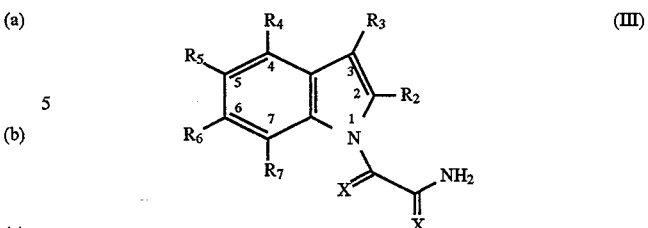

where each X is independently selected from oxygen and sulfur.

For formulae (I), (II), and (III) above the remaining groups are defined as follows:

$R_3$ is selected from groups (a), (b) and (c) where;
  (a) is $C_7$–$C_{20}$ alkyl, $C_7$–$C_{20}$ alkenyl, $C_7$–$C_{20}$ alkynyl, carbocyclic radicals, or heterocyclic radicals, or
  (b) is a member of (a) substituted with one or more independently selected non-interfering substituents; or
  (c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen; (that is, the $R_2$ radical may contain hydrogen atoms, but the remaining atoms comprising the total of 1 to 3 are non-hydrogen);

$R_6$ and $R_7$ are independently selected from hydrogen, a non-interfering substituent, or the group, —($L_a$)-(acidic group); wherein —($L_a$)—, is an acid linker having an acid linker length of 1 to 10; provided, that at least one of $R_6$ and $R_7$ must be the group, —($L_a$)-(acidic group);

$R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

Preferred Subgroups of Compounds of Formulae (I), (II), (III), and (IV):

A preferred subclass of compounds of formulae (I), (II), and (III) are those wherein all X are oxygen.

Another preferred subclass of compounds of formulae (I), (II), and (III) are those wherein $R_2$ is selected from the group; halo, cyclopropyl, methyl, ethyl, —O-methyl, and —S-methyl.

Another preferred subclass of compounds of formulae (I), (II) and (III) are those wherein for $R_3$, —(L)— is selected from the group consisting of:

—C≡C—,

—CH=CH—,

—CH$_2$—,

—(CH$_2$)$_2$—, $$-(CH_2)_3-\underset{O}{\underset{\|}{C}}-,$$

—(CH$_2$)$_s$—S—,

—(CH$_2$)$_s$—O—, and

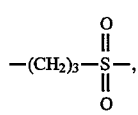

where s=0 or 1.

Another preferred subclass of compounds of formulae (I), (II), and (III) are those wherein for $R_3$, group $R_{80}$ is carbocyclic and is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

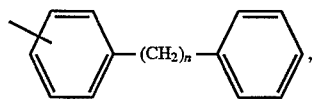

where n is a number from 1 to 8. Particularly preferred are compounds wherein $R_3$ is selected from the group consisting of

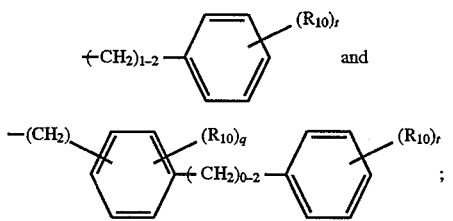

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5.

Another preferred subclass of compounds of formulae (I), (II), and (III) are those wherein $R_7$ is a substituent having an acid linker with an acid linker length of 2 or 3.

Another preferred subclass of compounds of formulae (I), (II), and (III) are those wherein $R_7$ comprises an acidic group and the acid linker for the acidic group has an acid linker length of 2 or 3 and the acid linker group, —($L_a$)—, for $R_7$ is selected from the group represented by the formula;

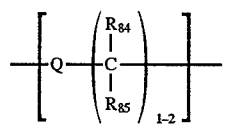

where Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, ethoxycarbonyl, and halo. Most preferred are compounds where the acid linker, —($L_a$)—, for $R_7$ is selected from the specific groups;

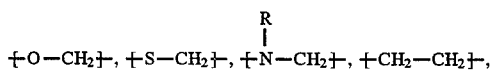

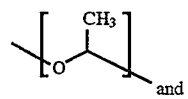

and

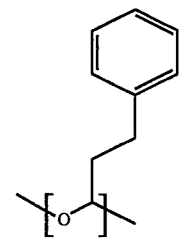

where R is H or $C_1$–$C_4$ alkyl.

Another preferred subclass of compounds of formulae (I), (II), and (III) are those wherein $R_6$ comprises an acidic group and the acid linker of the $R_6$ acidic group has an acid linker with an acid linker length of 3 to 10 atoms and the acid linker group, —($L_a$)—, for $R_6$ is selected from;

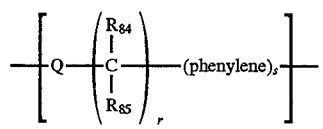

where r is a number from 1 to 7, s is 0 or 1, and Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, ethoxycarbonyl, and halo. Most preferred are compounds where the acid linker, —($L_a$)—, for $R_6$ is selected from the specific groups;

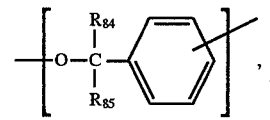

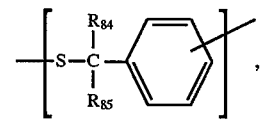

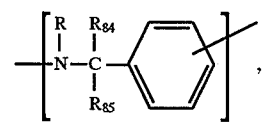

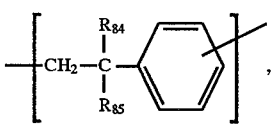

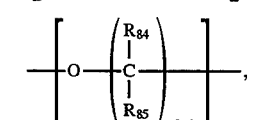

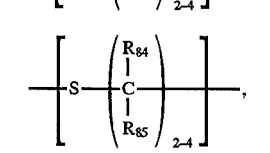

-continued

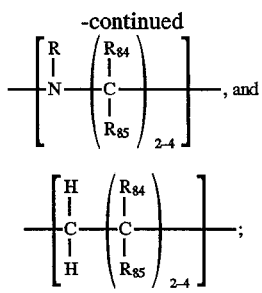

wherein; R is hydrogen or $C_1$–$C_4$ alkyl, $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, ethoxycarbonyl, and halo.

Another preferred subclass of compounds of formulae (I), (II), (III) are those wherein the acidic group (or salt, and prodrug derivatives thereof) on $R_6$ and/or $R_7$ is selected from the following:

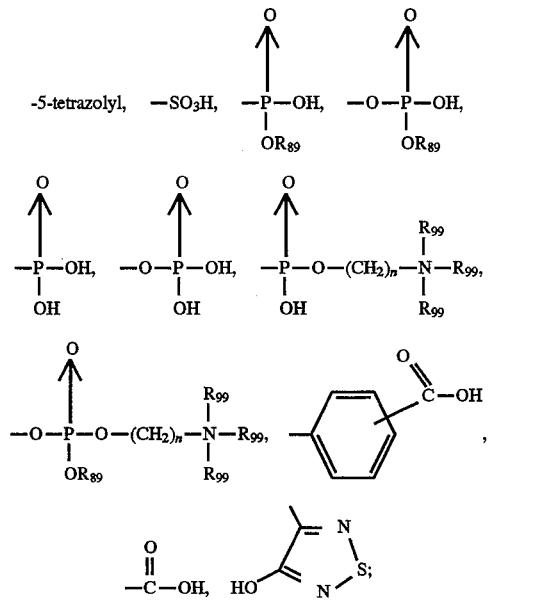

where n is 1 to 8, $R_{89}$ is a metal or $C_1$–$C_{10}$ alkyl, and $R_{99}$ is hydrogen or $C_1$–$C_{10}$ alkyl. Particularly preferred are compounds wherein the acidic group of $R_7$ or $R_8$ is selected from;

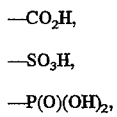

—$CO_2H$,

—$SO_3H$,

—$P(O)(OH)_2$, or salt, and prodrug (e.g., ester) derivatives thereof. The most preferred acidic group is carboxyl. It is highly preferred that only one of $R_6$ or $R_7$ contain an acidic group.

Another preferred subclass of compounds of formula (I) are those wherein $R_4$ and $R_5$ are each independently selected from hydrogen and non-interfering substituents, with the non-interfering substituents being selected from the group consisting of $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —$C(O)O(C_1$–$C_6$ alkyl), —$(CH_2)_n$—$O$—$(C_1$–$C_6$ alkyl), benzyloxy, phenoxy, phenylthio, —$(CONHSO_2R)$, —CHO, amino, amidino, bromo, carbamyl, carboxyl, ethoxycarbonyl, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

Preferred compounds of the invention are those having the general formula (IV), (V), or (VI);

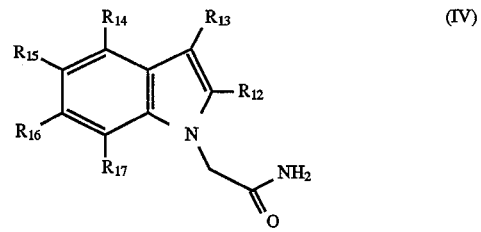

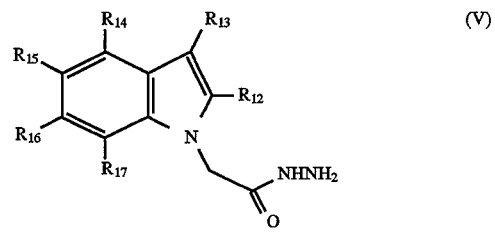

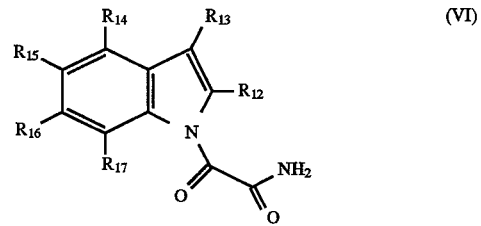

wherein for formulae (IV) (V) and (VI);

at least one of $R_{16}$ or $R_{17}$ must be —$(L_a)$-(acidic group); and $R_{13}$ is selected from groups (a), (b) and (c) where;

(a) is $C_7$–$C_{20}$ alkyl, $C_7$–$C_{20}$ alkenyl, $C_7$–$C_{20}$ alkynyl; or a carbocyclic radical selected from the group cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

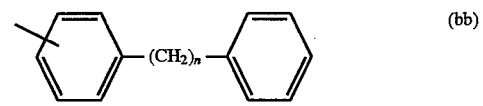

where n is a number from 1 to 8; or (b) is a member of (a) substituted with one or more independently selected non-interfering substituents selected from the group consisting of $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2-C_{12}$ alkylcarbonyl, $C_2-C_{12}$ alkylcarbonylamino, $C_2-C_{12}$ alkoxyamino, $C_2-C_{12}$ alkoxlaminocarbonyl, $C_1-C_{12}$ alkylamino, $C_1-C_6$ alkylthio, $C_2-C_{12}$ alkylthiocarbonyl, $C_1-C_6$ alkylsulfinyl, $C_1-C_6$ alkylsulfonyl, $C_2-C_6$ haloalkoxy, $C_1-C_6$ haloalkylsulfonyl, $C_1-C_6$ haloalkyl, $C_1-C_6$ hydroxyalkyl, —C(O)O($C_1-C_6$ alkyl), —(CH$_2$)$_n$—O—($C_1-C_6$ alkyl), benzyloxy, phenoxy, phenylthio, (—CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1-C_6$ carbonyl; where n is from 1 to 8; or (c) is the group —(L$_1$)—R$_{81}$; where, —(L$_1$)— is a divalent linking group having the formula;

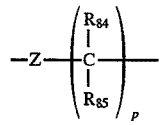

where,

R$_{84}$ and R$_{85}$ are each independently selected from hydrogen, $C_1-C_{10}$ alkyl, aryl, $C_1-C_{10}$ alkaryl, $C_1-C_{10}$ aralkyl, carboxy, ethoxycarbonyl, and halo;

p is 1 to 5,

Z is a bond, —(CH$_2$)—, —O—, —N($C_1-C_{10}$ alkyl)—, —NH—, or —S—; and where R$_{81}$ is a group selected from (a) or (b);

R$_{12}$ is hydrogen, halo, $C_1-C_3$ alkyl, $C_3-C_4$ cycloalkyl, $C_3-C_4$ cycloalkenyl, —O—($C_1-C_2$ alkyl , or —S—($C_1-C_2$ alkyl;

R$_{17}$ is selected from hydrogen, a non-interfering substituent, or the group, —(L$_a$)-(acidic group), wherein the acid linker —(L$_a$)— has an acid linker length of 2 or 3 atoms and is represented by the formula;

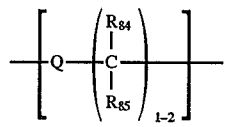

where Q is selected from the group —(CH$_2$)—, —O—, —NH—, and —S—; R$_{84}$ and R$_{85}$ are each independently selected from hydrogen, $C_1-C_{10}$ alkyl, aryl, $C_1-C_{10}$ alkaryl, $C_1-C_{10}$ aralkyl, hydroxy, and halo; and the acidic group is selected from

—CO$_2$H,

—SO$_3$H,

—P(O)(OH)$_2$,

R$_{16}$ is selected from hydrogen, a non-interfering substituent, or the group, —(L$_a$)-(acidic group), wherein the acid linker —(L$_a$)— has an acid linker length of 3 to 10 atoms and the acid linker group, —(L$_a$)— is;

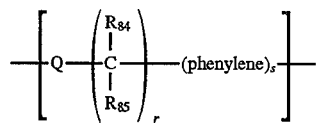

where r is a number from 1 to 7, s is 0 or 1, and Q is selected from the group —(CH$_2$)—, —O—, —NH—, and —S—; and R$_{84}$ and R$_{85}$ are each independently selected from hydrogen, $C_1-C_{10}$ alkyl, aryl, $C_1-C_{10}$ alkaryl, $C_1-C_{10}$ aralkyl, carboxy, ethoxycarbonyl, and halo; and the acidic group is selected from

—CO$_2$H,

—SO$_3$H,

—P(O)(OH)$_2$.

R$_{14}$ and R$_{15}$ are each independently selected from hydrogen, non-interfering substituents, selected from the group consisting of $C_1-C_6$ alkyl, $C_1-C_6$ alkenyl, $C_1-C_6$ alkynyl, $C_7-C_{12}$ aralkyl, $C_7-C_{12}$ alkaryl, $C_3-C_8$ cycloalkyl, $C_3-C_8$ cycloalkenyl, phenyl, toluyl, xylenyl, biphenyl, $C_1-C_6$ alkoxy, $C_1-C_6$ alkenyloxy, $C_1-C_6$ alkynyloxy, $C_2-C_{12}$ alkoxyalkyl, $C_2-C_{12}$ alkoxyalkyloxy, $C_2-C_{12}$ alkylcarbonyl, $C_2-C_{12}$ alkylcarbonylamino, $C_2-C_{12}$ alkoxyamino, $C_2-C_{12}$ alkoxyaminocarbonyl, $C_1-C_{12}$ alkylamino, $C_1-C_6$ alkylthio, $C_2-C_{12}$ alkylthiocarbonyl, $C_1-C_6$ aikylsulfinyl, $C_1-C_6$ alkylsulfonyl, $C_2-C_6$ haloalkoxy, $C_1-C_6$ haloalkylsulfonyl, $C_1-C_6$ haloalkyl, $C_1-C_6$ hydroxyalkyl, —C(O)O($C_1-C_6$ alkyl), —(CH$_2$)$_n$—O—($C_1-C_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1-C_6$ carbonyl; where n is from 1 to 8.

Another preferred class of compounds according to this invention are the compounds represented by formulae (IV), (V) and (VI) where the acid linker, —(L$_a$)—, for R$_{16}$ is selected from the groups;

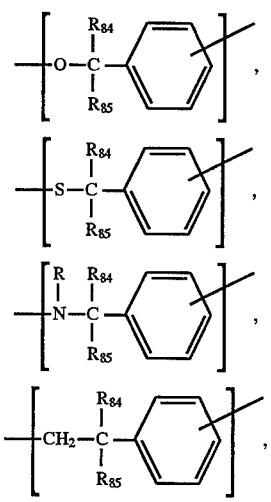

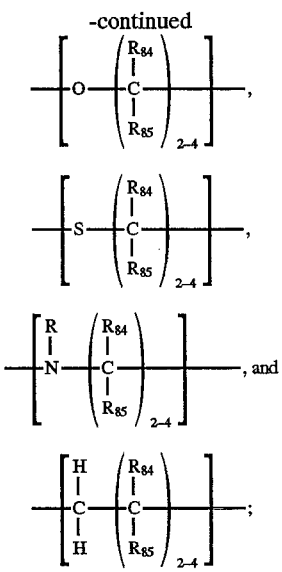

wherein; R is selected from hydrogen and $C_1$-$C_4$ alkyl; and $R_{84}$ and $R_{85}$ are each independently selected from hydrogen, $C_1$-$C_{10}$ alkyl, aryl, $C_1$-$C_{10}$ alkaryl, $C_1$-$C_{10}$ aralkyl, carboxy, ethoxycarbonyl, and halo.

Specific preferred compounds and all pharmaceutically acceptable salts, solvates and prodrug derivatives thereof which are illustrative of the compounds of the invention include the following:

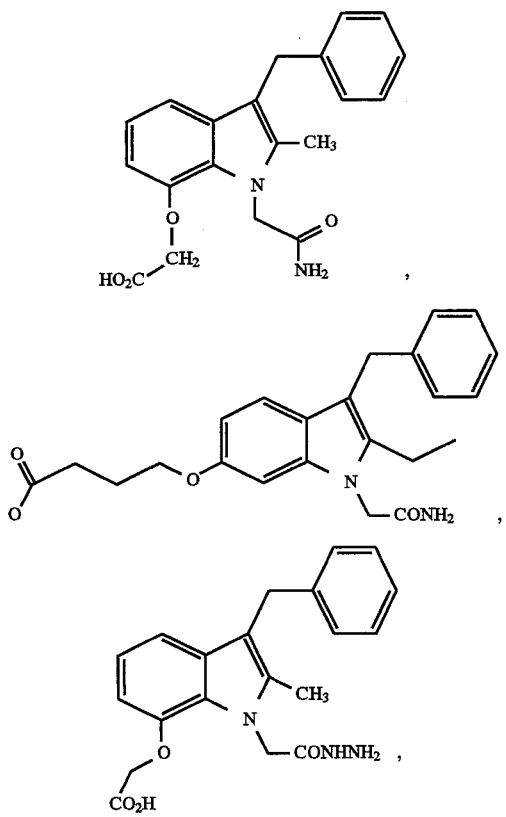

and mixtures of the above compounds in any combination.

The salts of the above 1H-indole-1-functional compounds represented by formulae (I), (II), (III), (IV), (V) and (VI) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66:1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmirate, pantothenate, phosphate, polygalacturonate, salicylate, stearate, subacetate, succinate, tannate, tartrate, rosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans- isomeric forms of the compounds. The R- and S- isomers and mixtures thereof, including racemic mixtures as well as mixtures of cis- and trans- isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. The prodrug derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

Synthesis Methods
Scheme 1
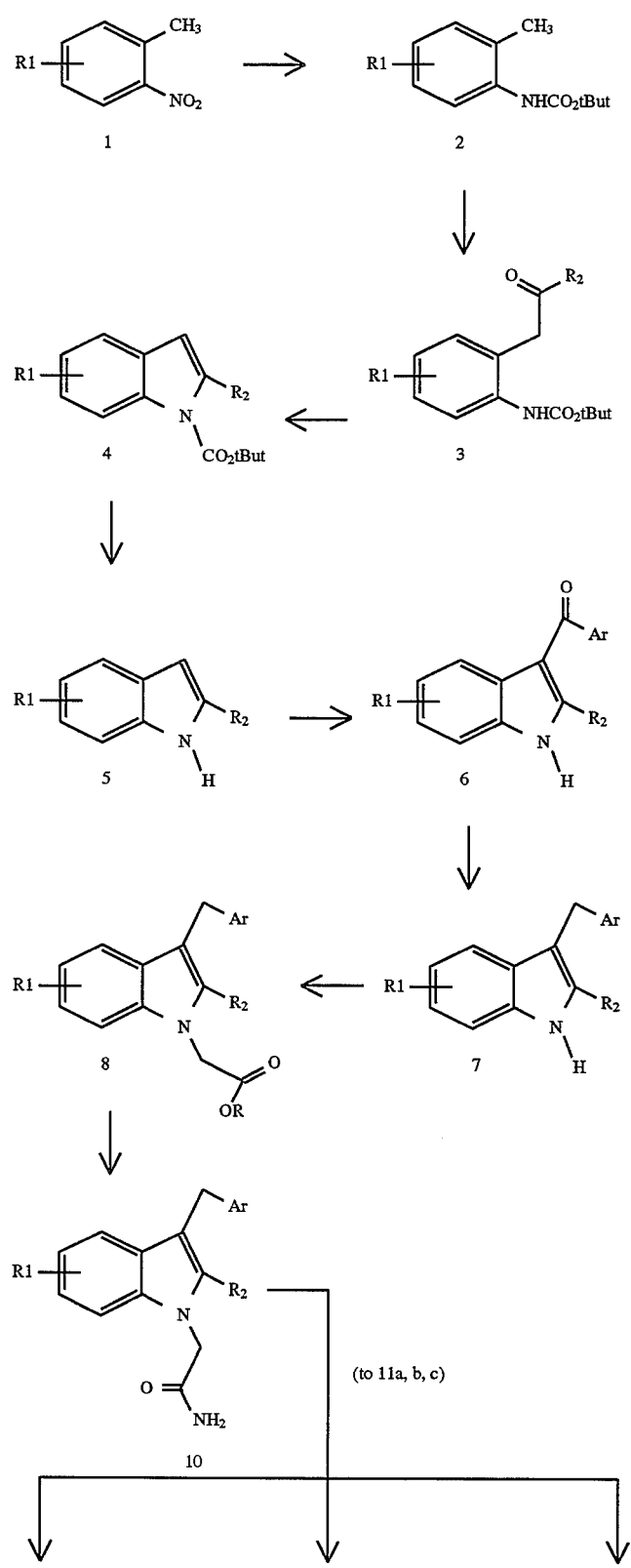

-continued
Synthesis Methods
Scheme 1

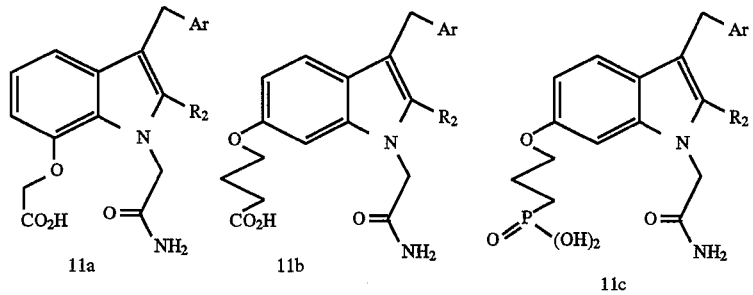

Indoles substituted at the 1-position by an alpha substituted acetamide are prepared using the reactions in Scheme 1. The orthonitrotoluene is reduced to the aniline by hydrogen in the presence of Pd/C. The aniline is then converted to 2 by heating with di-tert-butyl dicarbonate in tetrahydrofuran (THF). In the case where the R1 group of 2 is hydroxy, the hydroxy group is silylated using t-butyl dimethylsilyl chloride in DMF. The dilithium salt of the dianion of 2 is generated in THF using sec-butyl lithium and then reacted with an N-methoxy-N-methyl alkanamide to produce 3, which may be converted to 5 using TFA in $CH_2Cl_2$. Treatment of 3 with a more dilute solution of TFA in $CH_2Cl_2$ gives 4, which can be converted to 5 by warming with base. The conversion of 3 to 4 or 5 when R1 is OSiMe₂t-butyl also results in loss of the silyl group from R1 to give the hydroxy indole, which may be reprotected by alkylation of the sodium salt with benzyl bromide in DMF. Sequential treatment of the indoles 5 with n-butyl lithium, zinc chloride, and an aroyl halide affords the 3-acyl indoles 6, which are reduced to 7 by LAH in THF at room temperature. Alkylation of the sodium salt of the indoles 7 with an alkyl bromoacetate gives 8. The indoles 8 are reacted with $Me_2AlNH_2$ in benzene at 50° C. or are reacted with hydrazine, followed by reduction with Raney nickel to give 10. The R1 group of 10 is reduced to an hydroxy group, either by boron tribromide in $CH_2Cl_2$ in the case where R1 is methoxy or by hydrogenation in the presence off Pd/C when R1 is benzyloxy. The hydroxy 1-H-indole acetamide is then alkylated with an appropriate bromoalkyl ester or phosphonate in the presence of sodium hydride in DMF, followed by hydrolysis to the acid form such as 11a, 11b, and 11c.

Scheme 2

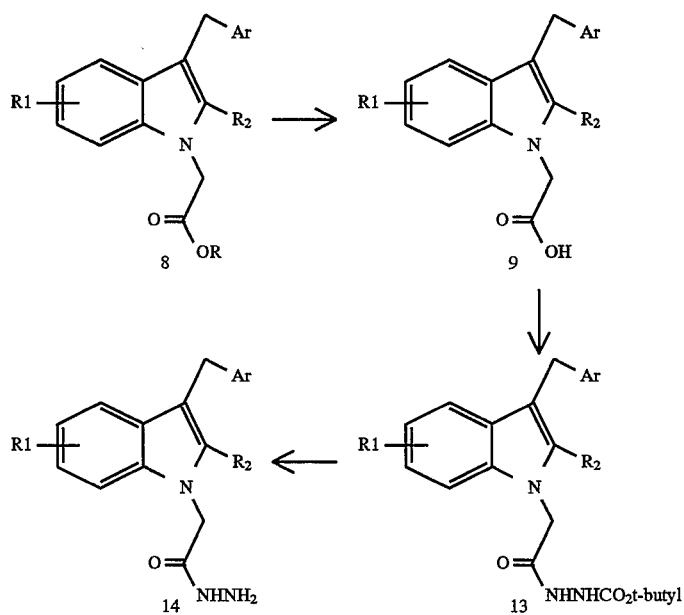

Indoles substituted at the 1-position with an alpha. substituted acetic acid hydrazide are prepared as in Scheme 2.

The diester 8, where R1 is $OCH_2CO_2Et$ and R is t-butyl is hydrolyzed to the N-acetic acid compound 9 using trifluoroacetic acid in $CH_2Cl_2$. Compound 9 is then reacted with methyl chloroformate and triethyl amine in $CH_2Cl_2$, followed by t-butyl carbazate to give the t-butoxycarbonyl protected hydrazide 13. Compound 13 is deesterified at R1 by stirring with 1N sodium hydroxide in ethanol, then the hydrazide is deprotected by stirring with trifluoroacetic acid in $CH_2Cl_2$ to give the 1-H-indole-1-hydrazide 14 as a trifluoroacetic acid salt.

Scheme 3

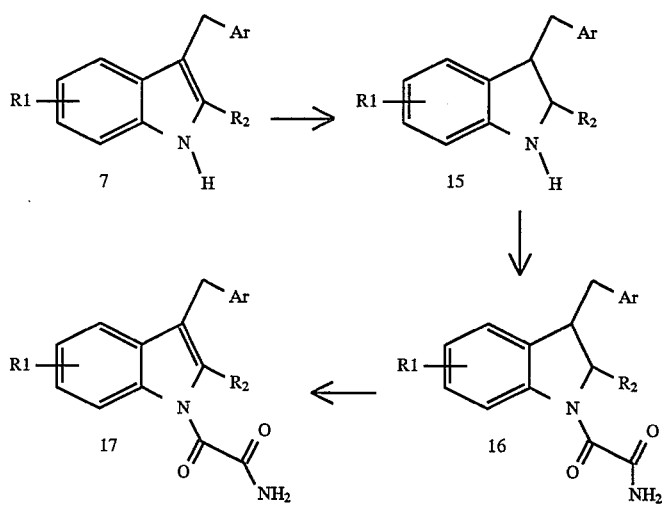

Indoles substituted at the 1-position with a glyoxylamide are prepared as in Scheme 3. The indoles 7 are reduced to the indolines 15 using $NaCNBH_3$ in HOAc. Treating 15 with oxalyl chloride followed by ammonia produces 16, which is subsequently oxidized by 2,3-dichloro-5,6-dicyano-1,4-benzoquinone (DDQ) in dioxane to give the 1H-indole-1-glyoxylamides 17.

EXAMPLES

Reference numbers in the following Examples (e.g., "R1", refer to compounds shown in the preceding Schemes.

Example 1

Preparation of [[1-(2-Amino-2-oxoethyl)-2-methyl-3-(phenylmethyl)-1H-indol-7-yl]oxy]acetic acid, a compound represented by the formula:

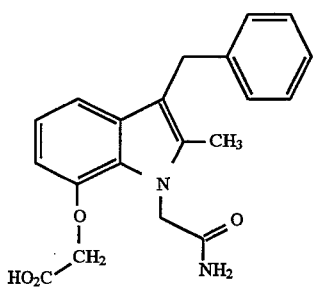

Part A Preparation of 2-Hydroxy-6-methyl-N-tert-butoxycarbonylaniline.

A suspension of 20 gm. (0.13 mol) of 2-hydroxy-6-methyl-nitrobenzene and 2.5 gm. of 10% Pd/C in 275 ml. of ethanol was shaken under hydrogen at 60 psi (414 kPa.) and room temperature for 2 hours. The mixture was filtered and evaporated in vacuo. The residue was dissolved in 300 ml. of tetrahydrofuran containing 25 gm. (0.12 mol) of tert-butyl dicarbonate, refluxed for 2 hours, cooled, and evaporated in vacuo. The residue was chromatographed on silica gel eluting with a gradient 20–100% Et2O/hexane to give 2 (R1=7-OH), 19.8 gm., 68% yield.

Analyses for $C_{12}H_{17}NO_3$: Calculated: C 64.56 H 7.68 N 6.27 Found: C 64.29 H 7.47 N 6.26

Part B Preparation of 2-tert-butyidimethylsilyloxy-6-methyl-N-tert-butoxycarbonyl aniline.

A solution of 10.4 gm. (47 mmol) of 2 (R1=7-OH), 3.4 gm. (50 mmol) of imidazole, and 7.6 gm. (50 mmol) of tertbutyldimethylsilyl chloride in 150 ml. of dimethylformamide was kept at room temperature for 20 hours, diluted with ethyl acetate, washed with water, washed with brine, dried over sodium sulfate, and evaporated in vacuo. The residue was chromatographed on silica gel eluting with a gradient 5–20% Et2O/hexane to give 2 (R1=7-OSiMe2t-butyl), 13.4 gm, 86%, Analyses for $C_{18}H_{31}NO_3Si$: Calculated: C 64.05 H 9.26 N 4.15 Found: C 64.29 H 9.02 N 4.30

Part C Preparation of 1-tert-butoxycarbonyl-2-methyl-7-hydroxy-1H-indole.

A solution of 25 gm. (74 mmol) of 2 (R1=7-OSiMe2t-butyl) in 400 ml. of tetrahydrofuran was cooled to –60° C. and treated with 143 ml. of 1.3M sec-butyl lithium in hexane. The mixture was allowed to warm to –20° C. and then recooled to –60° C. A solution of 8.2 gm. (80 mmol) of N-methyl-N-methoxyacetamide in 50 ml. of tetrahydrofuran was added slowly, the cooling bath was removed, the mixture stirred for 1.5 hours, diluted with water, and extracted with ethyl acetate. The organic phase was washed with brine, dried over sodium sulfate, and evaporated in vacuo to give 3 (R1=7-OSiMe2t-butyl, R2=MeCOCH2) as a residue which was dissolved in 125 ml. of dichloromethane and treated with 10 ml. of trifluoroacetic acid for 45 minutes. The solution was washed with aqueous sodium bicarbonate, washed with brine, dried over sodium sulfate, and evaporated in vacuo. The residue was chromatographed over silica gel eluting with a gradient 10–15% Et2O/hexane to give 4 (R1=7-OH, R2=Me), 10.3 gm., 70% yield.

Analyses for $C_{14}H_{17}NO_3$: Calculated: C 67.99 H 6.92 N 5.61 Found: C 66.31 H 6.83 N 5.87

Part D Preparation of 2-methyl-7-benzyloxy-1H-indole.

A solution of 10.3 gm. (42 mmol) of 4 (R1=7-OH, R2=Me), in 150 ml. of dimethylformamide and 20 ml. of tetrahydrofuran was treated with 1.8 gm. of sodium hydride (60% in mineral oil; 45 mmol) for 10 minutes and then with 5.5 ml. (46 mmol) of benzyl bromide for 3.5 hours, diluted with ethyl acetate, washed with water, washed with brine, dried over sodium sulfate, and evaporated in vacuo to give 4 (R1=7-benzyloxy, R2=Me) as a residue which was dissolved in 200 ml. of ethanol containing 50 ml of 5N sodium hydroxide, refluxed for 17 hours, cooled, acidified with 5N hydrochloric acid, and extracted with ethyl acetate. The organic phase was washed with brine, dried over sodium sulfate, and evaporated in vacuo. The residue was chromatographed on silica gel eluting with a gradient 10–20% Et$_2$O/hexane to give 5 (R1=7-OCH$_2$C$_6$H$_5$, R$_2$=Me), 7.7 gm., 78% yield.

Analyses for C$_{16}$H$_{15}$NO: Calculated: C 74.75 H 6.87 N 4.15 Found: C 75.03 H 6.66 N 4.24

Part E Preparation of 2-methyl-3-benzoyl-7-benzyloxy-1H-indole.

A solution 7.7 gm. (32 mmol) of 5 (R1=7-OCH$_2$C$_6$H$_5$, R2=Me) in 200 ml. of tetrahydrofuran was cooled to −5 C. and treated with 21 ml. of n-butyl lithium followed by 35 ml. of 1M zinc chloride in Et$_2$O, stirred 2.5 hours at room temperature, and evaporated in vacuo. The residue was dissolved in 200 ml. of toluene and treated with 4 ml. (34 mmol) of benzoyl chloride for 21 hours, stirred well with aqueous sodium bicarbonate and extracted with ethyl acetate. The organic phase was washed with brine, dried over sodium sulfate, and evaporated in vacuo. The residue was chromatographed on silica gel eluting with a gradient 20–50% Et$_2$O/hexane to give 6 (R1=7-OCH$_2$C$_6$H$_5$, R2=Me, Ar=C$_6$H$_5$), 4.6 gm., 43% yield, amorphous solid.

Analyses for C$_{23}$H$_{19}$NO$_2$: Calculated: C 80.92 H 5.61 N 4.10 Found: C 80.99 H 5.90 N 3.89

Part F Preparation of 2-methyl-3-phenylmethyl-7-benzyloxy-1H-indole.

A solution of 4.6 gm. (13 mmol) of 6 (R1=7-OCH$_2$C$_6$H$_5$, R2=Me, Ar=C$_6$H$_5$) in 200 ml. of tetrahydrofuran containing 2 gm. of lithium aluminum hydride was stirred for 19.5 hours, cooled in ice water, and decomposed by the sequential addition of ethyl acetate and then 5N sodium hydroxide. The solution was decanted, washed with brine, dried over sodium sulfate, and evaporated in vacuo. The residue was chromatographed on silica gel eluting with a gradient 5–15% Et$_2$O/hexane to give 7 (R1=7-OCH$_2$C$_6$H$_5$, R2=Me, Ar=C$_6$H$_5$), 3.4 gm., 77% yield, mp 124°–125° C./Et$_2$O-EtOH.

Analyses for C$_{23}$H$_{21}$NO: Calculated: C 84.37 H 6.46 N 4.28 Found: C 84.15 H 6.69 N 4.26

Part G Preparation of [2-methyl-3-(phenylmethyl)-7-benzyloxy-1H-indol-1-yl]acetic acid ethyl ester.

A solution of 1.3 gm. (3 mmol) of 7 (R1=7-OCH$_2$C$_6$H$_5$, R2=He, Ar=C$_6$H$_5$) in 70 ml. of dimethylformamide and 10 ml. of tetrahydrofuran was treated with 130 mg. of sodium hydride 60% in mineral oil; 3.3 mmol) for 15 minutes and then with 0.55 ml. (3.4 mmol) of ethyl bromoacetate for 1.25 hours, diluted with ethyl acetate, washed with water, washed with brine, dried over sodium sulfate, and evaporated in vacuo. The residue was chromatographed on silica gel eluting with a gradient 5–15% Et2O/hexane to give 8 (R1=7-OCH$_2$C$_6$H$_5$, R=Et, R2=Me, Ar=C$_6$H$_5$, X=OEt), 890 mg., 58% yield, mp 92°–93° C./CH$_2$Cl$_2$-EtOH.

Analyses for C$_{27}$H$_{27}$NO$_3$: Calculated: C 78.42 H 6.58 N 3.39 Found: C 78.63 H 6.55 N 3.36

Part H Preparation of [2-methyl-3-(phenylmethyl)-7-benzyloxy-1H-indol-1-yl]acetamide.

A solution of 880 mg. (2.2 mmol) of 8 (R1=7-OCH$_2$C$_6$H$_5$, R=Et, R$_2$=Me, Ar=C$_6$H$_5$, X=OEt) in 40 ml. of benzene was treated with 15 ml. of a ca. 0.67M solution of Me$_2$AlNH$_2$ in 2:1 benzene:toluene at 50° C. for 21 hours, cooled in ice-water, decomposed with ice-1N hydrochloric acid, and extracted with ethyl acetate. The organic phase was washed with brine, dried over sodium sulfate, and evaporated in vacuo. The residue was chromatographed on silica gel eluting with Et$_2$O and then ethyl acetate to give 10 (R1=7-OCH$_2$C$_6$H$_5$, R2=Me, Ar=C$_6$H$_5$, X=NH$_2$), 650 mg., 80% yield, mp 167°–168° C./EtOAc.

Analyses for C$_{25}$H$_{24}$N$_2$O$_2$: Calculated: C 78.10 H 6.29 N 7.29 Found: C 77.36 H 6.50 N 7.07

Part I Preparation of [2-Methyl-3-(phenylmethyl)-7-hydroxy-1H-indol-1-yl]acetamide:

A mixture of 0.5 gm. of 10% Pd/C and 625 mg. of 10 (R1=7-OCH$_2$C$_6$H$_5$, R2=Me, Ar=C$_6$H$_5$, X=NH$_2$) in 75 ml. of tetrahydrofuran and 75 ml. of ethanol was shaken under 42–47 psi (289–324 KPa.) of hydrogen for 5.5 hours, filtered, and evaporated in vacuo. The residue was chromatographed on silica gel eluting with ethyl acetate to give 10 (R1=7-OH, R2=Me, Ar=C$_6$H$_5$, X=NH$_2$), 370 mg., 77% yield, mp 189°–191° C./EtOAc.

Analyses for C$_{18}$H$_{18}$N$_2$O$_2$: Calculated: C 73.45 H 6.16 N 9.52 Found: C 73.28 H 6.30 N. 9.33

Part J Preparation of [[1-(2-Amino-2-oxoethyl)-2-methyl-3-(phenylmethyl)-1H-indol-7-yl]oxy]acetic acid tert-butyl ester, compound represented by the formula:

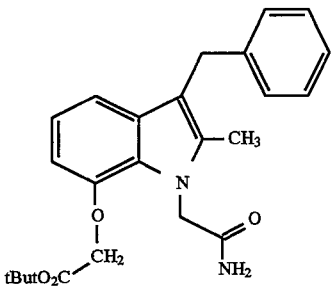

A solution of 370 mg. (1.3 mmol) of 10 (R1=7-OH, R$_2$=Me, Ar=C$_6$H$_5$, X=NH$_2$) in 70 ml. of dimethylformamide and 10 ml. of tetrahydrofuran was treated with 60 mg. of sodium hydride (69% in mineral oil; 1.5 mmol) for 15 minutes and then with 0.25 ml. of tert-butyl bromoacetate for 2.5 hours, diluted with ethyl acetate, washed with water, washed with brine, dried over sodium sulfate, and evaporated in vacuo to give 10 (R1=-OCH$_2$CO$_2$t-butyl, R2-Me, Ar=C$_6$H$_5$, X=NH$_2$), 340 mg., 66% yield, mp 113°–115° C./Et$_2$O-hexane.

Analyses for C$_{24}$H$_{28}$N$_2$O$_4$: Calculated: C 70.57 H 6.91 N 6.86 Found: C 70.33 H 7.02 N 6.76

Part K Preparation of [[1-(2-amino-2-oxoethyl)-2-methyl-3-(phenylmethyl)-1H-indol-7-yl]oxy]acetic acid.

A solution of 340 mg. of 10 (R1=7-OCH$_2$CO$_2$t-butyl, R2=Me, Ar=C$_6$H$_5$, X=NH$_2$) in 30 ml. of dichloromethane and 2–3 ml. of trifluoroacetic acid was stirred 2.5 hours and then evaporated in vacuo to give 11a (R2=Me, Ar=C$_6$H$_5$, X=NH$_2$), 220 mg., 76% yield, mp 190°–192° C./EtOAc.

Analyses for C$_{20}$H$_{20}$N$_2$O$_4$: Calculated: C 68.17 H 5.72 N 7.95 Found: C 68.42 H 5.84 N 8.09

Example 2

This Example illustrates the preparation of an acetamide compound with the acidic group in the 6 position.

Preparation of 4-[[1-(2-amino-2-oxoethyl)-2-ethyl-3-(phenylmethyl)-1H-indol-6-yl]oxy]butyric acid, a compound represented by the formula:

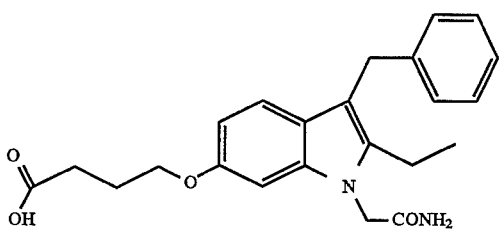

Part A Preparation of N-tert-butoxycarbonyl-2-methyl-5-methoxyaniline.

A mixture of 10 gm. (60 mmol) of 3-nitro-4-methylanisole and 4 gm. of 10% Pd/C was stirred under 1 atm. of hydrogen for 30 hours, filtered, and evaporated in vacuo to give 3-amino-4-methylanisole as a residue which was dissolved in 250 ml. of tetrahydrofuran containing 13 gm. (60 mmol) of tert-butyl dicarbonate, refluxed for 3 hours, cooled, and evaporated in vacuo. The residue was chromatographed on silica gel eluting with a gradient 5–10% $Et_2O$/hexane to give 2 (R1=5-OMe), 10.3 gm., 72% yield, mp 72°–74° C.

Analyses for $C_{13}H_{19}NO_3$: Calculated: C 65.80 H 8.07 N 5.90 Found: C 65.55 H 8.00 N 6.00

Part B Preparation of 2-ethyl-6-methoxy-1H-indole.

A solution of 5.4 gm. (23 mmol) of 2 (R1=5-OMe) in 150 ml. of tetrahydrofuran was cooled to –75° C. and treated slowly with 36 ml. of sec-butyl lithium (1.3M in hexane; 47 mmol), allowed to warm to –20 C., recooled to –75° C., and treated slowly with a solution of 2.9 gm. (25 mmol) of N-methyl-N-methoxypropranamid in 50 ml. of tetrahydrofuran, stirred without cooling for 25 minutes, diluted with water, and extracted with ethyl acetate. The organic phase was washed with brine, dried over sodium sulfate, and evaporated in vacuo to give 3 (R1=5-OMe, R2=Et), as a residue. The residue was dissolved in 125 of dichloromethane and 10 ml. of trifluoroacetic acid, stirred 10 minutes, washed with aqueous sodium bicarbonate, washed with brine, dried over sodium sulfate, and evaporated in vacuo to give to give 4 (R1=6-OMe, R2=Et) as a residue which was dissolved in 50 ml. of ethanol containing 5 ml. of 5N sodium hydroxide, refluxed 2.5 hours, cooled, acidified with 5N hydrochloric acid, and extracted with ethyl acetate. The organic phase was washed with brine, dried over sodium sulfate, and evaporated in vacuo. The residue was chromatographed on silica gel eluting with a gradient 15–20% $Et_2O$/hexane to give 5 R1=6-OMe, R2=Et), 840 mg., 21% yield, mp 77°–79° C./$Et_2O$-hexane.

Analyses for $C_{11}H_{13}NO$: Calculated: C 75.40 H 7.48 N 7.99 Found: C 75.18 H 7.53 N 7.99

Part C Preparation of 2-ethyl-3-benzoyl-6-methoxy-1H-indole.

A solution of 840 mg. (4.8 mmol) of 5 (R1=6-OMe, R2=Et) in 100 ml. of tetrahydrofuran was treated sequentially with 3.0 ml. of 1.6M n-butyl lithium/hexane and 5.0 ml. of 1.0M $ZnCl_2/Et_2O$ at –5° C., stirred at room temperature for 2 hours, evaporated in vacuo, dissolved in 100 ml. of toluene, and treated with 0.6 ml. of benzoyl chloride for 17.5 hours. The mixture was stirred well with aqueous sodium bicarbonate and extracted with ethyl acetate. The organic phase was washed with brine, dried over sodium sulfate, and evaporated in vacuo. The residue was chromatographed on silica gel eluting with a gradient 20–60% $Et_2O$/hexane to give 6 (R1=6-OMe, R2=Et, Ar=$C_6H_5$), 435 mg., 33% yield, mp 167–169/$CH_2Cl_2$-EtOH.

Analyses for $C_{18}H_{17}NO_2$: Calculated: C 77.40 H 6.13 N 5.01 Found: C 77.70 H 6.27 N 5.28

Part D Preparation of 2-ethyl-3-(phenylmethyl)-6-methoxy-1H-indole.

A solution of 435 mg. of 6 (R1=6-OMe, R2=Et, Ar=$C_6H_5$) in 75 ml. of tetrahydrofuran containing 0.4 gm. of lithium aluminum hydride was stirred for 24 hours, cooled in ice-water, and decomposed by the sequential addition of ethyl acetate and 5N sodium hydroxide. The solution was decanted, washed with brine, dried over sodium sulfate, and evaporated in vacuo. The residue was chromatographed on silica gel eluting with a gradient 10–25% $Et_2O$/hexane to give 7 (R1=6-OMe, R2=Et, Ar=$C_6H_5$), 160 mg., 38% yield, mp 101°–103° C./$Et_2O$-hexane.

Analyses for $C_{18}H_{19}NO$: Calculated: C 81.48 H 7.22 N 5.28 Found: C 81.31 H 7.85 N 5.30

Part E Preparation of [2-ethyl-3-(phenylmethyl)-6-methoxy-1H-indol-1-yl]acetic acid methyl ester.

To a solution of 1.59 g. (6 mmol) of 7 (R1=6-OMe, R2=Et, Ar=$C_6H_5$) in 15 ml. of dimethyl formamide was added 240 mg. (6 mmol) of 60% sodium hydride/mineral oil. Stirred at room temperature for 80 min., then added 0.57 ml. (6 mmol) of methyl. bromoacetate and continued to stir for 22 hours. Water and ethyl acetate were added. The ethyl acetate layer was separated, washed with brine, dried over magnesium sulfate and evaporated in vacuo. The residue was chromatographed on silica gel, eluting with 20% EtOAc/hexane to give 8 (R1=6-OMe, R=Me, R2=Et, Ar=$C_6H_5$), 931 mg., 46% yield, mp 90°–94° C.

Analyses for $C_{21}H_{23}NO_3$: Calculated: C 74.75 H 6.87 N 4.15 Found: C 73.83 H 6.90 N 4.04

Part F Preparation of [2-ethyl-3-(phenylmethyl)-6-methoxy-1H-indol-1-yl]acetic acid hydrazide A solution of 1.33 g. (3.9 mmol) of 8 (R1=6-OMe, R=Me, R2=Et, Ar=$C_6H_5$) in 20 ml. of ethanol containing 4 ml. of hydrazine was heated at reflux for 4 hours. The solution was evaporated to dryness in vacuo. The residue was dissolved in EtOAc/$H_2O$. The ethyl acetate layer was separated, washed with brine, dried over magnesium sulfate and evaporated in vacuo. The residue was crystallized from methanol to give [2-ethyl-3-(phenylmethyl)- 6-methoxy-1H-indol-1-yl]acetic acid hydrazide (R1=6-OMe, R2=Et, Ar=$C_6H_5$), 1.05 g., 80% yield, mp 164°–166° C.

Analyses for $C_{20}H_{23}N_3O_2$: Calculated: C 71.19 H 6.87 N 12.45 Found: C 72.15 H 7.06 N 12.92

Part G Preparation of [2-ethyl-3-(phenylmethyl)-6-methoxy-1H-indol-1-yl]acetamide A suspension of 688 mg. (2 mmol) of [2-ethyl-3-(phenylmethyl)-6-methoxy-1H-indol-1-yl]acetic acid hydrazide (from Part F, R=6-OMe, R2=Et, Ar=$C_6H_5$) and approximately 700 mg. of Raney nickel in 25 ml. of ethanol was heated at reflux for 1.5 hours. The ethanol solution was decanted from the Raney nickel, then the Raney nickel was washed 3 times with methylene chloride, each time decanting the wash solution into the ethanol solution. The combined organics were filtered free of residual. Raney nickel, then evaporated in vacuo. The residue was dissolved in ethyl acetate containing 10% methanol and washed with water and brine, then dried over magnesium sulfate and evaporated in vacuo to give 10 (R1=6-OMe, R2=Et, Ar=$C_6H_5$), 566 mg., 88% yield, mp 190°–192° C.

Analyses for $C_{20}H_{22}N_2O_2$: Calculated: C 74.51 H 6.88 N 8.69 Found: C 74.23 H 6.91 N 8.91

Part H Preparation of [2-ethyl-3-(phenylmethyl)-6-hydroxy-1H-indol-1-yl]acetamide To a solution of 551 mg. (1.7 mmol) of 10 (R1=6-OMe, R2=Et, Ar=$C_6H_5$) in 30 ml. of methylene chloride was added 6 ml. of a 1M solution of boron tribromide in methylene chloride (6 mmol). The solution was stirred for 4 hours, then an additional 1.5 ml. of the boron tribromide solution was added. After stirring an additional 2.5 hours, the solution was evaporated to dryness in vacuo. The residue was dissolved in ethyl acetate and washed with water and brine, then dried over magnesium sulfate and evaporated in vacuo. The product, 10 (R1=6-OH, R2=Et, Ar=$C_6H_5$) was crystallized from methanol, yielding 422 mg., 80% yield, mp 215°–217° C.

Analyses for $C_{19}H_{20}N_2O_2$: Calculated: C 74.00 H 6.54 N 9.08 Found: C 73.79 H 6.80 N 8.92

Part I Preparation of 4-[[1-(2-amino-2-oxoethyl)-2-ethyl-3-(phenylmethyl)-1H-indol-6-yl]oxy]butyric acid ethyl ester To a suspension of 24 mg.(0.6 mmol) of 60% sodium hydride/mineral oil in 15 ml. of dimethyl formamide was added 185 mg. (0.6 mmol) of 10 (R1=6-OH, R2=Et, Ar=$C_6H_5$). The suspension was stirred 2 hours at room temperature, then there was added 0.09 ml. (0.6 mmol) of ethyl-4-bromobutyrate, stirred for 3.5 hours, then there was added water and ethyl acetate. The ethyl acetate layer was separated, washed with brine, dried over magnesium sulfate, and evaporated in vacuo. The residue was chromatographed over silica gel, eluting with 50% EtOAc/hexane followed by EtOAc to give 10 (R1=6-O$CH_2CH_2CH_2CO_2$Et, R2=Et, Ar=$C_6H_5$), 70 mg., 28% yield, mp 105°–119° C.

Analyses for $C_{25}H_{30}N_2O_4$: Calculated: C 71.07 H 7.16 N 6.63 Found: C 72.54 H 7.53 N 6.93

Part J Preparation of 4-[[1-(2-amino-2-oxoethyl)-2-ethyl-3-(phenylmethyl)-1H-indol-6-yl]oxy]butyric acid A suspension of 60 mg.(0.14 mmol) of 10 (R1=6-O$CH_2CH_2CH_2CO_2$Et, R2=Et, Ar=$C_6H_5$) in 3 ml. of methanol and 1 ml. of 1N sodium hydroxide was heated to give a complete solution, then stirred at room temperature for 1 hour. Ethyl acetate and water were added to the reaction mixture. The ethyl acetate layer was removed and the aqueous layer was acidified to pH 2.5 with 1N hydrochloric acid and extracted with ethyl acetate. The ethyl acetate extract was washed with brine, dried over magnesium sulfate and evaporated in vacuo. The residue was stirred with methanol and filtered off to give 11b (R1=6-O$CH_2CH_2CH_2CO_2$H, R2=Et, Ar=$C_6H_5$), 40mg., 73% yield, mp 174°–176° C.

Analyses for $C_{23}H_{26}N_2O_4$: Calculated: C 70.03 H 6.64 N 7.10 Found: C 70.35 H 6.60 N 7.33

Example 3

Preparation of [3-[[1-(2-amino-2-oxoethyl)-2-ethyl-3-(phenylmethyl)-1H-indol-6-yl]oxy]propyl]phosphonic acid, a compound represented by the formula:

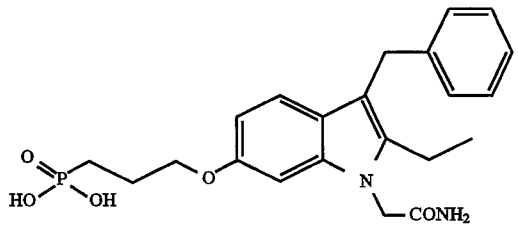

Part A Preparation of [3-[[1-(2-amino-2-oxoethyl)-2-ethyl-3-(phenylmethyl)-1H-indol-6-yl]oxy]propyl]phosphonic acid dimethyl ester To a suspension of 29 mg. (0.71 mmol) of 60% sodium hydride/mineral oil in 5 ml of dimethylformamide was added 219 mg. (0.71 mmol) of 10 (R1=6-OH, R2=Et, Ar=$C_6H_5$) in 5 ml of dimethylformamide. Stirred for 30 minutes at room temperature, then added 196 mg. (0.85 mmol) of 3-bromopropylphosphonic acid dimethyl ester. Stirred for 2 hours, then added water and ethyl acetate. The ethyl acetate layer was separated, washed with brine, dried over magnesium sulfate, and evaporated in vacuo. The residue was chromatographed on silica gel, eluting with EtOAc followed by 5% MeOH/EtOAc to give 10 (R1=6-O$CH_2CH_2CH_2PO_3Me_2$, R2=Et, Ar=$C_6H_5$), 248 mg., 76%, mp 118°–119° C.

Analyses for $C_{24}H_{31}N_2O_5P$: Calculated: C 62.87 H 6.32 N 6.11 Found: C 63.12 H 6.74 N 6.10

Part B Preparation of [3-[[1-(2-amino-2-oxoethyl)-2-ethyl-3-(phenylmethyl)-1H-indol-6-yl]oxy]propyl]phosphonic acid A solution of 240 mg.(0.52 mmol) of 10 (R1=6-O$CH_2CH_2CH_2PO_3Me2$, R2=Et, Ar=$C_6H_5$) and 0.55 ml (4.19 mmol) of bromotrimethylsilane in 5 ml of methylene chloride was stirred for 16 hours. The reaction mixture was concentrated at reduced pressure, 5 ml methanol added, stirred 1 hour, and concentrated. The residue was crystallized from EtOAc/MeCN/HOAc/H2O to give 167 mg, 75% yield of 11c, mp 183°–186° C.

Analyses for $C_{22}H_{27}N_2O_5P$: Calculated: C 61.39 H 6.32 N 6.51 Found: C 61.61 H 6.06 N 6.27

Example 4

Preparation of [[1-(2-hydrazino-2-oxoethyl)-2-methyl-3-(phenylmethyl)-1H-indol-7-yl]oxy]acetic acid, a compound represented by the formula:

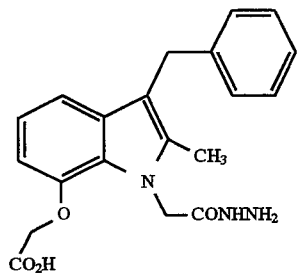

Part A Preparation of [[1-(2-hydroxy-2-oxoethyl)-2-methyl-3-(phenylmethyl)-1H-indol-7-yl]oxy]acetic acid ethyl ester.

A solution of 460 mg. (1.05 mmol of [[1-(2-tertbutyloxy-2-oxoethyl)-2-methyl-3-(phenylmethyl)-1H-indol-7-yl]oxy] acetic acid ethyl ester 8 in 10 ml of methylene chloride and 2 ml of trifluoroacetic acid was stirred at room temperature for 2.5 hours. The solvent and excess trifluoroacetic acid were evaporated in vacuo. The residue was dissolved in ethyl acetate and washed with water and brine, then dried over $MgSO_4$ and evaporated to give 396 mg. (99% yield) of 9 (R1=7-O$CH_2CO_2$Et, R2=Me, Ar=$C_6H_5$) as an oil.

Analyses for $C_{22}H_{23}NO_5$: Calculated: C 69.28 H 6.08 N 3.67 Found: C 69.03 H 6.27 N 3.71

Part B Preparation of [[1-[2-(2-tert-butoxycarbonylhydrazino)-2-oxoethyl]-2-methyl-3-(phenylmethyl)-1H-indol-7-yl]oxy]acetic acid ethyl ester.

To a solution of 381 mg. (1 mmol) of 9 (R1=7-O$CH_2CO_2$Et, R2=Me, Ar=$C_6H_5$) in 50 ml. of methylene chloride was added 0.16 ml. (1.2 mmol) of triethylamine. The solution was cooled to −5° C. and 0.1 ml. (1.3 mmol) of methyl chloroformate was added. The solution was stirred for 5 min., then 132 mg. (1 mmol) of tertbutyl carbazate was added and the mixture stirred at room temperature for 30 min. The solution was washed with water and brine, then dried over $MgSO_4$ and evaporated. The residue was chromatographed on silica gel, eluted with 50% EtOAc/hexane to give 428 mg. (86% yield) of [[1-(2-N- tertbutyloxycarbonylhydrazino-2-oxoethyl)-2-methyl-3-(phenylmethyl)-1H-indol-7-yl]oxy]acetic acid ethyl ester 13 as an oil.

Analyses for $C_{27}H_{33}N_3O_6$: Calculated: C 65.44 H 6.71 N 8.48 Found: C 65.58 H 6.87 N 8.30

Part C Preparation of [[1-(2-hydrazino-2-oxoethyl)-2-methyl-3-(phenylmethyl)-1H-indol-7-yl]oxy]acetic acid.

A solution of 380 mg. of 1-(2-tertbutyloxycarbonylhydrazino-2-oxoethyl)-2-methyl-3-(phenylmethyl)-1H-indol-7-yl]oxy]acetic acid ethyl ester 13 in 15 ml of ethanol and 4 ml of 1N NaOH was stirred at room temperature for 1 hour. The solution was diluted with water and extracted with ethyl acetate, washed with brine, dried (HgSO$_4$) and evaporated. The residue was stirred with 5 ml of trifluoroacetic acid for 1 hour. The solution was evaporated in vacuo and the residue was dissolved in EtOAc/H$_2$O. The EtOAc extract was separated, washed with brine, dried over MgSO$_4$ and evaporated to give a solid. The solid was stirred with ether and filtered off to give 143 mg. (51% yield) of 14 (R1=7-OCH$_2$CO$_2$H, R2=Me, Ar=C$_6$H$_5$) as a trifluoroacetic acid salt.

Analyses for $C_{22}N_{22}F_3N_3O_6$: Calculated: C 54.89 H 4.60 N 8.73 Found: C 56.03 H 5.04 N 8.89

Therapeutic Use of 1H-indole-1-functional compounds 1H-indole-1-functional compounds described herein are believed to achieve their beneficial therapeutic action principally by direct inhibition of human sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting sPLA$_2$ with an therapeutically effective amount cf 1H-indole-1-functional compound corresponding to Formulae (I), (II), (III), (IV), (IV), or (VI) substituted am the 6 or 7 positions with an acidic derivative, its salt or a prodrug derivative thereof.

The compounds of the invention may be used in a method of treating a mammal (e.g., a human) to alleviate the pathological effects of septic shock, adult respiratory distress syndrome, pancreatitus, trauma, bronchial asthma, allergic rhinitis, and rheumatoid arthritis; wherein the method comprises administrating to the mammal at least one 1H-indole-1-functional compound represented by formulae (II), (II), (III), (IV), (V) or (VI) or any combination thereof in a therapeutically effective amount. A therapeutically effective amount is an amount sufficient to inhibit sPLA$_2$ mediated release of fatty acid and to thereby inhibit or prevent the arachidonic acid cascade and its deleterious products. The therapeutic amount of compound of the invention needed to inhibit sPLA$_2$ may be readily determined by taking a sample of body fluid and assaying it for sPLA$_2$ content by conventional methods.

Pharmaceutical Formulations of the Invention

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the 1H-indole-1-functional compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable Tarrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or a pharmaceutically acceptable salt, solvate, or prodrug thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
|---|---|
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred no a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture: is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |

31

-continued

| Color | q.v. |
|---|---|
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

Assay Experiments

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:

REACTION BUFFER $CaCl_2.2H_2O$ (1.47 g/L)

KCl (7.455 g/L)

Bovine Serum Albumin (fatty acid free) (1 g/L) (Sigma A-7030, product of Sigma Chemical Co. St. Louis Mo., USA)

TRIS HCl (3.94 g/L)

pH 7.5 (adjust with NaOH)

ENZYME BUFFER 0.05 $NaOAc.3H_2O$, pH 4.5

0.2 NaCl

Adjust pH to 4.5 with acetic acid

DTNB—5,5'-dithiobis-2-nitrobenzoic acid

RACEMIC DIHEPTANOYL THIO—PC racemic 1,2-bis(heptanoylthio)-1,2-dideoxy-sn-glycero-3-phosphorylcholine TRITON X-100™ prepare at 6.249 mg/ml in reaction buffer to equal 10 uM.

REACTION MIXTURE

A measured volume of racemic diheptanoyl thio PC supplied in chloroform at a concentration of 100 mg/ml is taken to dryness and redissolved in 10 millimolar TRITON X 100™ nonionic detergent aqueous solution. Reaction Buff added to the solution, then DTNB to give the Reaction Mixture.

The reaction mixture thus obtained contains 1 m diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested am a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

| Results of Human Secreted Phospholipase $A_2$ Inhibition Tests | |
|---|---|
| Compound of Example number | Inhibition of human secreted $PLA_2$ µM $IC_{50}$ ± mean deviation (3–4 tests) |
| 1 (acid form of acetamide) | 0.013 ± 0.002 |
| 2 (acid form of acetamide) | 0.033 ± 0.003 |
| 3 (acid form of acetamide) | 0.035 ± 0.008 |
| 4 (acid form of hydrazide) | 0.20 ± 0.09 |

Assay Example 2

Method:

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer ( Model FTO3C, product of Grass Medical Instruments Co., Quincy, Mass., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative concentration-response curves:

Initially tissues were challenged 3 times with KCl (40 mM) to test tissue viability and to obtain a consistent response. After recording the maximal response to KCl, the Elssues were washed and allowed to return to baseline before the next challenge. Cumulative concentration-response curves were obtained from pleural strips by increasing the agonist concentration (sPLA$_2$) in the tissue bath by half-log$_{10}$ increments while the previous concentration remained in contact with the tissues (Ref.1, supra.) Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of sPLA$_2$, the compounds and their respective vehicles were added to the tissues 30 min. prior to starting the sPLA$_2$ concentration-response curves.

Statistical analysis;

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the ED$_{50}$ for the control curve, the steepness of the curves, and the PA$_2$, the concentration of antagonist that requires a two-fold increase in agonist to achieve an equivalent response. The Schild slope was determined to be 1, using statistical nonlinear modeling methods similar to those described by Waud 1976), Equation 27, p. 164 (Ref. 2). The Schild slope equal to 1 indicates the model is consistent with the assumptions of a competitive antagonist; therefore, the pA2 may be interpreted as the apparent K$_B$, the dissociation constant of the inhibitor.

To estimate the drug-induced suppression of the maximal responses, sPLA$_2$ responses (10 ug/ml) were determined in the absence and presence of drug, and percent suppression was calculated for each pair of tissues. Representative examples of inhibitory activities are presented in Table 2, below.

Ref. 1—van, J. M.: Cumulative dose-response curves. II. Technique for the making of dose-response curves in isolated organs and the evaluation of drug parameters. *Arch. Int. Pharmacodyn. Ther.*, 143: 299–330, 1963.

Ref. 2—Waud, D.: Analysis of dose-response relationships. in *Advances in General and Cellular Pharmacology* eds Narahashi, Bianchi 1:145–178, 1976.

Results of Human Secreted Phospholipase A$_2$ Inhibition Tests on guinea pig lung tissue

TABLE II

| Compound of Example No. | Tissue test secreted PLA$_2$ Apparent K$_B$ μM |
| --- | --- |
| 1 | 0.39 ± 0.12 |
| 2 | 1.47 ± 0.34 |

TABLE II-continued

| Compound of Example No. | Tissue test secreted PLA$_2$ Apparent K$_B$ μM |
| --- | --- |
| 3 | 0.415 ± 0.051 |
| 4 | 1.67 ± 0.28 |

While the present invention has been illustrated above by certain specific embodiments, in is not intended that these specific examples should limit the scope of the invention as described in the appended claims.

We claim:

1. A 1H-indole-1-acetamide compound or a pharmaceutically acceptable salt or solvate derivative thereof; wherein said compound is represented by the formula;

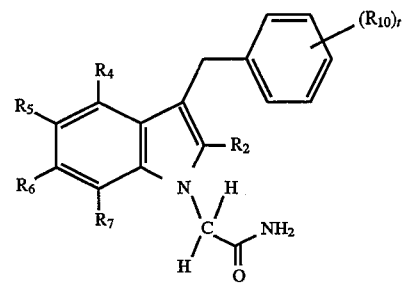

wherein;

R$_2$ is cyclopropyl, methyl, or ethyl;

R$_6$ and R$_7$ are independently selected from hydrogen or a non-interfering substituent selected from the group consisting of C$_1$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, toluyl, xylenyl, biphenyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_1$–C$_6$ haloalkoxy, C$_1$–C$_6$ haloalkylsulfonyl, C$_1$–C$_6$ haloalkyl, C$_1$–C$_6$ hydroxyalkyl, —C(O)O(C$_1$–C$_6$ alkyl), —(C(CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl where n is from 1 to 8; or the group —(L$_a$)-(acidic group); where —(L$_a$)—, is an acid linker having an acid linker length of 1 to 10; provided, that at least one of R$_6$ and R$_7$ must be the group, —(L$_a$)-(acidic group);

R$_4$ and R$_5$ are each independently selected from hydrogen or a non-interfering substituent selected from the group consisting of C$_1$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, toluyl, xylenyl, biphenyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkylamino, C$_2$–C$_{12}$ alkoxyaminocarbonyl, C$_1$–C$_{12}$ alkylamino, C$_1$–C$_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$— O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl where n is from 1 to 8; or a carbocyclic radical or carbocyclic radical substituted with said non-interfering substituents, said carbocyclic radical selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

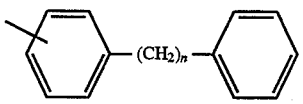
(bb)

where n is a number from 1 to 8; or a heterocyclic radical or a heterocyclic radical substituted with said non-interfering substituents, said heterocyclic radical selected from the group consisting of pyrrolyl, furanyl, thiophenyl, pyrazolyl, imidazolyl, phenylimidazolyl, triazolyl, isoxaxolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1,2-A)pyridinyl, benzotriazolyl, anthranilyl, 1,2-benzisoxazolyl, benzoxazolyl, benzothiazolyl, purinyl, pyridinyl, dipyridinyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl; and $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, and t is a number from 0 to 5.

2. The compound of claim 1 wherein;

(i) X is oxygen;

(ii) $R_2$ is selected from the group; halo, cyclopropyl, methyl, and ethyl;

(iii) $R_3$ has as a linking group —(L)— an alkylene chain of 1 or 2 carbon atoms and $R_{80}$ is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

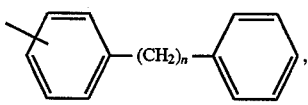
(bb)

where n is a number from 1 to 8;

(iv) $R_6$ or $R_7$ have an (acidic group) on the group —$(L_a)$-(acidic group) selected from:

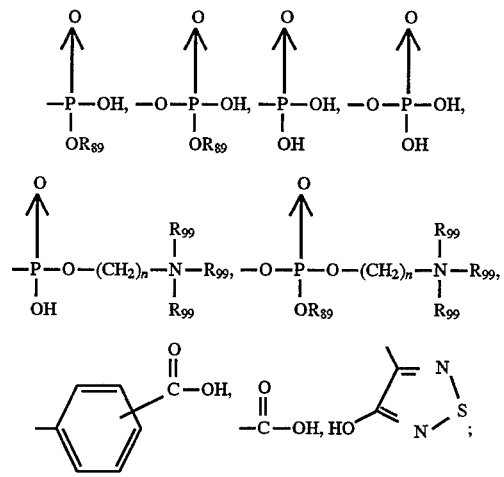

where n is 1 to 8, $R_{89}$ is a metal or $C_1$–$C_{10}$ alkyl, and $R_{99}$ is hydrogen or $C_1$–$C_{10}$ alkyl; and (v) $R_4$ and $R_5$ are each independently selected from hydrogen and non-interfering substituents, with the non-interfering substituents being selected from the group consisting of the following: $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3$, thioacetal thiocarbonyl, and $C_1$–$C_6$ carbonyl; where n is from 1 to 8.

3. The compound of claim 2, wherein, (A) for (iii), the group $R_3$ is selected from the group consisting of

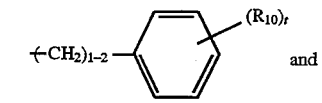
and
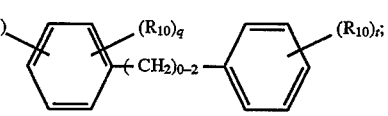

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5; and (B) for (iii) the linking group —(L)— of $R_3$ is selected from the group consisting of:

—C≡C—,

—CH=CH—,

—CH$_2$—,

—(CH$_2$)$_2$—,

—(CH$_2$)$_3$—C—,
$\quad\quad\quad\quad\ \ \ $‖
$\quad\quad\quad\quad\ \ \ $O

—(CH$_2$)$_s$—S—,

—(CH$_2$)$_s$—O—, and $\quad\quad\quad\quad$O
$\quad\quad\quad\quad$‖
—(CH$_2$)$_3$—S—,
$\quad\quad\quad\quad$‖
$\quad\quad\quad\quad$O where s=0 or 1;

(C) for (iv) the (acidic group) of R$_6$ or R$_7$ is selected from:

—CO$_2$H,

—SO$_3$H,

—P(O)(OH)$_2$.

4. The compound of claim 1 wherein R$_7$ comprises an acidic group and has an acid linker with an acid linker length of 2 or 3 and the acid linker group, —(L$_a$)—, for R$_7$ is represented by the formula;

$$\left[Q-\left(\begin{array}{c}R_{84}\\|\\C\\|\\R_{85}\end{array}\right)_{1-2}\right]$$

where Q is selected from the group —(CH$_2$)—, —O—, —NH—, and —S—, and R$_{84}$ and R$_{85}$ are each independently selected from hydrogen, C$_1$-C$_{10}$ alkyl, aryl, C$_1$-C$_{10}$ alkaryl, C$_1$-C$_{10}$ aralkyl, carboxy, ethoxycarbonyl, and halo.

5. The compound of claim 4 wherein R$_7$ comprises an acidic group and the acid linker group, —(L$_a$)—, for R$_7$ is selected from the group consisting of;

$\{$O—CH$_2\}$, $\{$S—CH$_2\}$, $\{$CH$_2$—CH$_2\}$, $\{$N—CH$_2\}$,
$\quad\quad\quad\quad\quad\quad\quad\quad\quad\quad\quad\quad\quad\quad\quad\quad\quad\ $|
$\quad\quad\quad\quad\quad\quad\quad\quad\quad\quad\quad\quad\quad\quad\quad\quad\quad\ $R

[structures with CH$_3$ and phenethyl groups] and where R is H or C$_1$-C$_4$ alkyl.

6. The compound of claim 1 wherein R$_6$ comprises an acidic group and has an acid linker with an acid linker length of 3 to 10 atoms and the acid linker group, —(L$_a$)—, for R$_6$ is selected from;

$$\left[Q-\left(\begin{array}{c}R_{84}\\|\\C\\|\\R_{85}\end{array}\right)-(\text{phenylene})_s\right]_r$$

where r is a number from 1 to 7, s is 0 or 1, and Q is selected from the group —(CH$_2$)—, —O—, —NH—, and —S—, and R$_{84}$ and R$_{85}$ are each independently selected from hydrogen, C$_1$-C$_{10}$ alkyl, aryl, C$_1$-C$_{10}$ alkaryl, C$_1$-C$_{10}$ aralkyl, carboxy, ethoxycarbonyl, and halo.

7. The compound of claim 6 wherein the acid linker, —(L$_a$)—, for R$_6$ is selected from group consisting of;

$$\left[O-\underset{\underset{R_{85}}{|}}{\overset{\overset{R_{84}}{|}}{C}}-\text{phenylene}\right],$$

$$\left[S-\underset{\underset{R_{85}}{|}}{\overset{\overset{R_{84}}{|}}{C}}-\text{phenylene}\right],$$

$$\left[\underset{\underset{R}{|}}{N}-\underset{\underset{R_{85}}{|}}{\overset{\overset{R_{84}}{|}}{C}}-\text{phenylene}\right],$$

$$\left[CH_2-\underset{\underset{R_{85}}{|}}{\overset{\overset{R_{84}}{|}}{C}}-\text{phenylene}\right],$$

$$\left[O-\left(\begin{array}{c}R_{84}\\|\\C\\|\\R_{85}\end{array}\right)_{2-4}\right],$$

$$\left[S-\left(\begin{array}{c}R_{84}\\|\\C\\|\\R_{85}\end{array}\right)_{2-4}\right],$$

$$\left[\underset{\underset{R}{|}}{N}-\left(\begin{array}{c}R_{84}\\|\\C\\|\\R_{85}\end{array}\right)_{2-4}\right], \text{ and}$$

$$\left[\underset{\underset{H}{|}}{\overset{\overset{H}{|}}{C}}-\left(\begin{array}{c}R_{84}\\|\\C\\|\\R_{85}\end{array}\right)_{2-4}\right];$$

wherein; R is hydrogen or C$_1$-C$_4$ alkyl, R$_{84}$ and R$_{85}$ are each independently selected from hydrogen, C$_1$-C$_{10}$ alkyl, aryl, C$_1$-C$_{10}$ alkaryl, C$_1$-C$_{10}$ aralkyl, carboxy, ethoxycarbonyl, and halo.

8. A 1H-indole-1-hydrazide compound or a pharmaceutically acceptable salt or solvate derivative thereof; wherein said compound is represented by the formula;

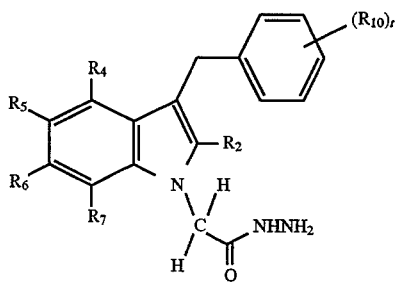

wherein:

R$_2$ is cyclopropyl, methyl, or ethyl;

R$_6$ and R$_7$ are independently selected from hydrogen or a non-interfering substituent selected from the group consisting of C$_1$–C$_6$ alkyl, C$_2$–C$_6$alkenyl, C$_2$–C$_6$ alkenyl, C$_7$–C$_{12}$ aralkyl, C$_7$–C$_{12}$ alkaryl, C$_3$–C$_8$ cycloalkyl, C$_3$–C$_8$ cycloalkenyl, phenyl, toluyl, xylenyl, biphenyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_1$–C$_6$ haloalkoxy, C$_1$–C$_6$ haloalkylsulfonyl, C$_1$–C$_6$ haloalkyl, C$_1$–C$_6$ hydroxyalkyl, —C(O)O(C$_1$–C$_6$ alkyl), —(CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl where n is from 1 to 8; or the group —(L$_a$)-(acidic group); where —(L$_a$)—, is an acid linker having an acid linker length of 1 to 10; provided, that at least one of R$_6$ and R$_7$ must be the group, —(L$_a$)-(acidic group);

R$_4$ and R$_5$ are each independently selected from hydrogen or a non-interfering substituent selected from the group consisting of C$_1$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, toluyl, xylenyl, biphenyl, C$_1$–C$_6$ alkoxy, C$_2$–C$_6$alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_1$–C$_6$ haloalkoxy, C$_1$–C$_6$ haloalkylsulfonyl, C$_1$–C$_6$ haloalkyl, C$_1$–C$_6$ hydroxyalkyl, —C(O)O(C$_1$–C$_6$ alkyl), —(CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl where n is from 1 to 8; or a carbocyclic radical or carbocyclic radical substituted with said non-interfering substituents, said carbocyclic radical selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

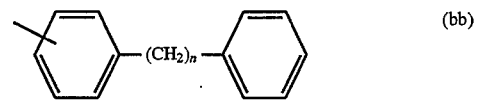

(bb)

where n is a number from 1 to 8; or a heterocyclic radical or a heterocyclic radical substituted with said non-interfering substituents said heterocyclic radical selected from the group consisting of pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1,2-A) pyridinyl, benzotriazolyl, anthranilyl, 1,2-benzisoxazolyl, benzoxazolyl, benzothiazolyl, purinyl, pyridinyl, dipyridinyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl; and R$_{10}$ is a radical independently selected from halo, C$_1$–C$_{10}$ alkyl, C$_1$–C$_{10}$ alkoxy, —S—(C$_1$–C$_{10}$ alkyl), and C$_1$–C$_{10}$ haloalkyl, and t is a number from 0 to 5.

9. The compound of claim 8 wherein;

(i) X is oxygen;

(ii) R$_2$ is selected from the group; halo, cyclopropyl, methyl, and ethyl;

(iii) R$_3$ has as a linking group —(L)— an alkylene chain of 1 or 2 carbon atoms and R$_{80}$ is selected from the group consisting of cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

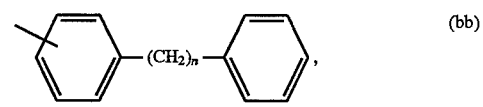

(bb)

where n is a number from 1 to 8;

(iv) R$_6$ or R$_7$ have an (acidic group) on the group —(L$_a$)-(acidic group) selected from:

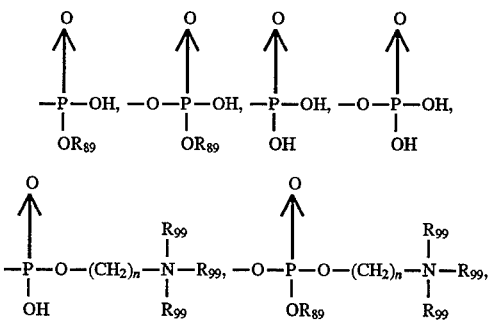

-continued

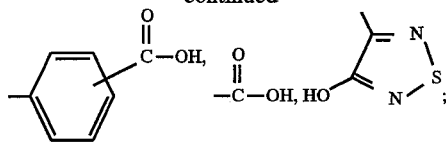

where n is 1 to 8, $R_{89}$ is a metal or $C_1$–$C_{10}$ alkyl, and $R_{99}$ is hydrogen or $C_1$–$C_{10}$ alkyl; and (v) $R_4$ and $R_5$ are each independently selected from hydrogen and non-interfering substituents, with the non-interfering substituents being selected from the group consisting of the following: $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —$(CH_2)_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

10. The compound of claim 9, wherein, (A) for (iii), the group $R_3$ is selected from the group consisting of

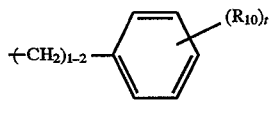

and

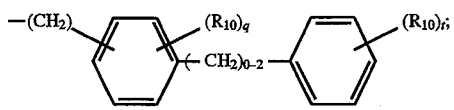

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5; and (B) for (iii) the linking group —(L)— of $R_3$ is selected from the group consisting of:

—C≡C—,

—CH=CH—,

—CH$_2$—,

—(CH$_2$)$_2$—,

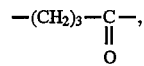

—(CH$_2$)$_s$—S—,

—(CH$_2$)$_s$—O—, and

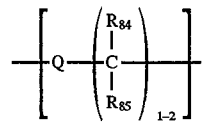

(C) for (iv) the (acidic group) of $R_6$ or $R_7$ is selected from:

—CO$_2$H,

—SO$_3$H,

—P(O)(OH)$_2$.

11. The compound of claim 8 wherein $R_7$ comprises an acidic group and has an acid linker with an acid linker length of 2 or 3 and the acid linker group, —($L_a$)—, for $R_7$ is represented by the formula;

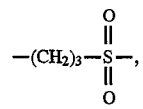

where Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, ethoxycarbonyl, and halo.

12. The compound of claim 11 wherein the acid linker group, —($L_a$)—, for $R_7$ is selected from the group consisting of;

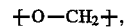

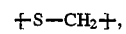

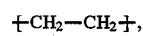

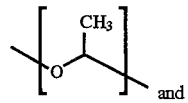

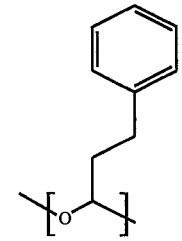

where R is H or $C_1$–$C_4$ alkyl.

13. The compound of claim 8 wherein $R_6$ comprises an acidic group and has an acid linker with an acid linker length of 3 to 10 atoms and the acid linker group, —($L_a$)—, for $R_6$ is selected from;

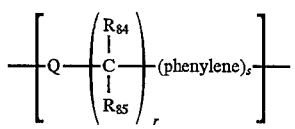

where r is a number from 1 to 7, s is 0 or 1, and Q is selected from the group —(CH$_2$)—, —O—, —NH—, and —S—, and R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy, ethoxycarbonyl, and halo.

14. The compound of claim 13 wherein the acid linker, —(L$_a$)—, for R$_6$ is selected from group consisting of;

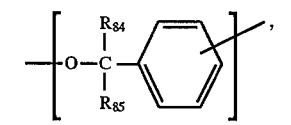
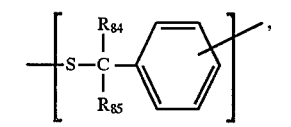
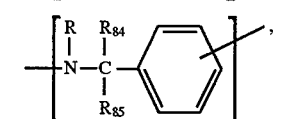
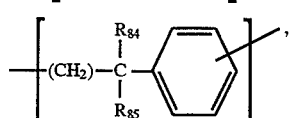
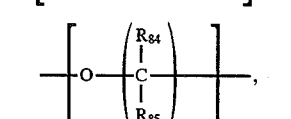
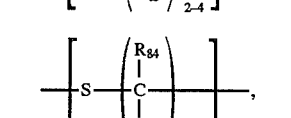
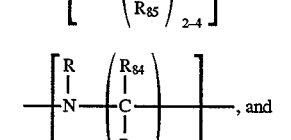
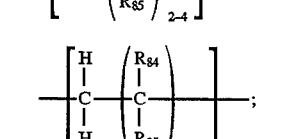

wherein; R is hydrogen or C$_1$–C$_4$ alkyl, R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy, ethoxycarbonyl, and halo.

15. A 1H-indole-1-acetamide compound or a pharmaceutically acceptable salt or solvate thereof; wherein said compound is represented by the formula (IV);

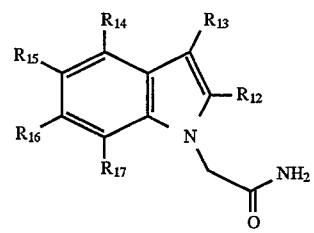

wherein;

R$_{13}$ is selected from groups (a), (b) and (c) where;
  (a) is C$_7$–C$_{20}$ alkyl, C$_7$–C$_{20}$ alkenyl, C$_7$–C$_{20}$ alkynyl; or a carbocyclic radical selected from the group cycloalkyl, cycloalkenyl, phenyl, naphthyl, norbornanyl, bicycloheptadienyl, toluyl, xylenyl, indenyl, stilbenyl, terephenylyl, diphenylethylenyl, phenyl-cyclohexenyl, acenaphthylenyl, and anthracenyl, biphenyl, bibenzylyl and related bibenzylyl homologues represented by the formula (bb),

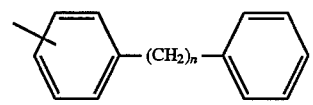

where n is a number from 1 to 8; or
  (b) is a member of (a) substituted with one or more independently selected non-interfering substituents selected from the group consisting of C$_1$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, toluyl, xylenyl, biphenyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_2$–C$_6$ haloalkoxy, C$_1$–C$_6$ haloalkylsulfonyl, C$_1$–C$_6$ haloalkyl, C$_1$–C$_6$ hydroxyalkyl, —C(O)O(C$_1$–C$_6$ alkyl), —(CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where R is H or C$_1$–C$_4$ alkyl and n is from 1 to 8;
  (c) is the group —(L$_1$)—R$_{81}$; where, —(L$_1$)— is a divalent linking group having the formula;

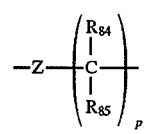

where,
R$_{84}$ and R$_{85}$ are each independently selected from hydrogen, C$_1$–C$_{10}$ alkyl, carboxyl, ethoxycarbonyl, or halo;
p is 1 to 5,
Z is a bond, —(CH$_2$)—, —O—, —N(C$_1$–C$_{10}$ alkyl) —, —NH—, or —S—; and
where R$_{81}$ is a group selected from (a) or (b);

$R_{12}$ is hydrogen, halo, $C_1$-$C_3$ alkyl, $C_3$-$C_4$ cycloalkyl, $C_3$-$C_4$ cycloalkenyl, —O—($C_1$-$C_2$ alkyl), or —S—($C_1$-$C_2$ alkyl);

$R_{17}$ is selected from hydrogen, a non-interfering substituent, or the group, —($L_a$)-(acidic group), wherein the acid linker —($L_a$)— has an acid linker length of 2 or 3 atoms and is represented by the formula;

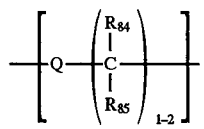

where Q is selected from the group —($CH_2$)—, —O—, —NH—, and —S—; $R_{84}$ and $R_{85}$ are each independently selected from hydrogen, $C_1$-$C_{10}$ alkyl, aryl, $C_1$-$C_{10}$ alkaryl, $C_1$-$C_{10}$ aralkyl, hydroxy, and halo; and the acidic group is selected from

—$CO_2H$,

—$SO_3H$,

—$P(O)(OH)_2$, $R_{16}$ is selected from hydrogen or a non-interfering substituent selected from the group consisting of $C_1$-$C_6$ alkyl, $C_2$-$C_6$ alkenyl, $C_2$-$C_6$ alkynyl, $C_7$-$C_{12}$ aralkyl, $C_7$-$C_{12}$ alkaryl, $C_3$-$C_8$ cycloalkyl, $C_3$-$C_8$ cycloalkenyl, phenyl, toluyl, xylenyl, biphenyl, $C_1$-$C_6$ alkoxy, $C_2$-$C_6$ alkenyloxy, $C_2$-$C_6$ alkynyloxy, $C_2$-$C_{12}$ alkoxyalkyl, $C_2$-$C_{12}$ alkoxyalkyloxy, $C_2$-$C_{12}$ alkylcarbonyl, $C_2$-$C_{12}$ alkylcarbonylamino, $C_2$-$C_{12}$ alkoxyamino, $C_2$-$C_{12}$ alkoxyaminocarbonyl, $C_1$-$C_{12}$ alkylamino, $C_1$-$C_6$ alkylthio, $C_2$-$C_{12}$ alkylthiocarbonyl, $C_1$-$C_6$ alkylsulfinyl, $C_1$-$C_6$ alkylsulfonyl, $C_2$-$C_6$ haloalkoxy, $C_1$-$C_6$ haloalkylsulfonyl, $C_1$-$C_6$ haloalkyl, $C_1$-$C_6$ hydroxyalkyl, —C(O)O($C_1$-$C_6$ alkyl), —($CH_2$)$_n$—O—($C_1$-$C_6$ alkyl), benzyloxy, phenoxy, phenylthio, —(CONHSO$_2$R), —CHO, amino, amidino, bromo, carbamyl, carboxyl, ethoxycarbonyl, —($CH_2$)$_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$-$C_6$ carbonyl, where R is H or $C_1$-$C_4$ alkyl and n is from 1 to 8; or the group, —($L_a$)-(acidic group), wherein the acid linker —($L_a$)— has an acid linker length of 3 to 10 atoms and the acid linker group, —($L_a$)— is;

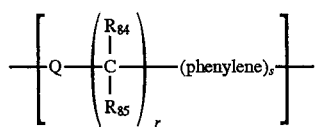

where r is a number from 1 to 7, s is 0 or 1, and Q is selected from the group —($CH_2$)—, —O—, —NH—, and —S—; and $R_{84}$ and $R_{85}$ are each independently selected from hydrogen, $C_1$-$C_{10}$ alkyl, aryl, $C_1$-$C_{10}$ alkaryl, $C_1$-$C_{10}$ aralkyl, carboxy, ethoxycarbonyl, and halo; and the acidic group is selected from

—$CO_2H$,

—$SO_3H$,

—$P(O)(OH)_2$, provided that at least one of $R_{16}$ or $R_{17}$ must be the group, —($L_a$)-(acidic group);

$R_{14}$ and $R_{15}$ are each independently selected from hydrogen or a non-interfering substituent selected from the group consisting of $C_1$-$C_6$ alkyl, $C_2$-$C_6$ alkenyl, $C_2$-$C_6$ alkynyl, $C_7$-$C_{12}$ aralkyl, $C_7$-$C_{12}$ alkaryl, $C_3$-$C_8$ cycloalkyl, $C_3$-$C_8$ cycloalkenyl, phenyl, toluyl, xylenyl, biphenyl, $C_1$-$C_6$ alkoxy, $C_2$-$C_6$ alkenyloxy, $C_2$-$C_6$ alkynyloxy, $C_2$-$C_{12}$ alkoxyalkyl, $C_2$-$C_{12}$ alkoxyalkyloxy, $C_2$-$C_{12}$ alkylcarbonyl, $C_2$-$C_{12}$ alkylcarbonylamino, $C_2$-$C_{12}$ alkoxyamino, $C_2$-$C_{12}$ alkoxyaminocarbonyl, $C_1$-$C_{12}$ alkylamino, $C_1$-$C_6$ alkylthio, $C_2$-$C_{12}$ alkylthiocarbonyl, $C_1$-$C_6$ alkylsulfinyl, $C_1$-$C_6$ alkylsulfonyl, $C_2$-$C_6$ haloalkoxy, $C_1$-$C_6$ haloalkylsulfonyl, $C_1$-$C_6$ haloalkyl, $C_1$-$C_6$ hydroxyalkyl, —C(O)O($C_1$-$C_6$ alkyl ), —($CH_2$)$_n$—O—($C_1$-$C_6$ alkyl), benzyloxy, phenoxy, phenylthio, —(CONHSO$_2$R), —CHO, amino, amidino, bromo, carbamyl, carboxyl, ethoxycarbonyl, —($CH_2$)$_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$-$C_6$ carbonyl; where R is H or $C_1$-$C_4$ alkyl and n is from 1 to 8.

16. A 1H-indole-1-acetic acid hydrazide compound or a pharmaceutically acceptable salt or solvate thereof; wherein said compound is represented by the formula (V):

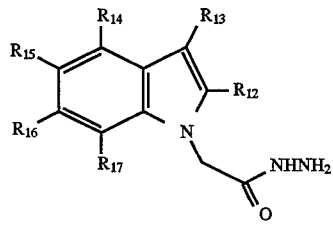

(V)

wherein;

$R_{13}$ is selected from groups (a), (b) and (c) where;
(a) is $C_7$-$C_{20}$ alkyl, $C_7$-$C_{20}$ alkenyl, $C_7$-$C_{20}$ alkynyl; or a carbocyclic radical selected from the group cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

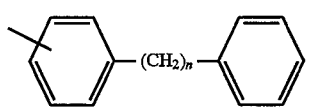

(bb)

where n is a number from 1 to 8; or
(b) is a member of (a) substituted with one or more independently selected non-interfering substituents selected from the group consisting of $C_1$-$C_6$ alkyl, $C_2$-$C_6$ alkenyl, $C_2$-$C_6$ alkynyl, $C_7$-$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where R is H or $C_1$–$C_4$ alkyl and n is from 1 to 8;

(c) is the group —(L$_1$)—R$_{81}$; where, —(L$_1$)— is a divalent linking group having the formula;

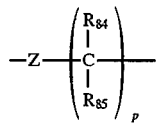

where,

R$_{84}$ and R$_{85}$ are each independently selected from hydrogen, $C_1$–$C_{10}$ alkyl, aryl, $C_1$–$C_{10}$ alkaryl, $C_1$–$C_{10}$ aralkyl, carboxy, ethoxycarbonyl, and halo;

p is 1 to 5,

Z is a bond, —(CH$_2$)—, —O—, —N($C_1$–$C_{10}$ alkyl)—, —NH—, or —S—; and where R$_{81}$ is a group selected from (a) or (b);

R$_{12}$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), or —S—($C_1$–$C_2$ alkyl);

R$_{17}$ is selected from hydrogen, a non-interfering substituent, or the group, —(L$_a$)-(acidic group), wherein the acid linker —(L$_a$)— has an acid linker length of 2 or 3 atoms and is represented by the formula;

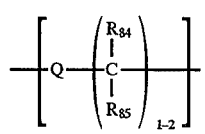

where Q is selected from the group —(CH$_2$)—, —O—, —NH—, and —S—; R$_{84}$ and R$_{85}$ are each independently selected from hydrogen, $C_1$–$C_{10}$ alkyl, aryl, $C_1$–$C_{10}$ alkaryl, $C_1$–$C_{10}$ aralkyl, hydroxy, and halo; and the acidic group is selected from

—CO$_2$H,

—SO$_3$H,

—P(O)(OH)$_2$,

R$_{16}$ is selected from hydrogen or a non-interfering substituent selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl, where R is H or $C_1$–$C_4$ alkyl and n is from 1 to 8; or the group, —(L$_a$)-(acidic group), wherein the acid linker —(L$_a$)— has an acid linker length of 3 to 10 atoms and the acid linker group, —(L$_a$)— is;

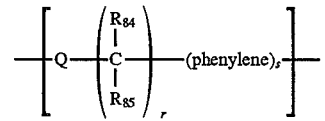

where r is a number from 1 to 7, s is 0 or 1, and Q is selected from the group —(CH$_2$)—, —O—, —NH—, and —S—; and R$_{84}$ and R$_{85}$ are each independently selected from hydrogen, $C_1$–$C_{10}$ alkyl, aryl, $C_1$–$C_{10}$ alkaryl, $C_1$–$C_{10}$ aralkyl, carboxy, ethoxycarbonyl, and halo; and the acidic group is selected from

—CO$_2$H,

—SO$_3$H,

—P(O)(OH)$_2$, provided that at least one of R$_{16}$ or R$_{17}$ must be the group, —(L$_a$)-(acidic group);

R$_{14}$ and R$_{15}$ are each independently selected from hydrogen or a non-interfering substituent selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where R is H or C$_1$–C$_4$ alkyl and n is from 1 to 8.

17. A pharmaceutical formulation comprising a 1H-indole-1-acetamide as claimed in claim 1 together with a pharmaceutically acceptable carrier or diluent therefor.

18. A pharmaceutical formulation comprising a 1H-indole-1-hydrazide as claimed in claim 8 together with a pharmaceutically acceptable carrier or diluent therefor.

19. A method of treating a mammal to alleviate the pathological effects of septic shock, adult respiratory distress syndrome, pancreatitis, trauma, bronchial asthma, allergic rhinitis, and rheumatoid arthritis; wherein the method comprises administration to said mammal of at least one 1H-indole-1-acetamide as claimed in claim 1 in an amount sufficient to inhibit sPLA$_2$ mediated release of fatty acid and to thereby inhibit or prevent the arachidonic acid cascade and its deleterious products.

20. A method of treating a mammal to alleviate the pathological effects of septic shock, adult respiratory distress syndrome, pancreatitis, trauma, bronchial asthma, allergic rhinitis, and rheumatoid arthritis; wherein the menhod comprises administration to said mammal of at least one 1H-indole-1-acetic acid hydrazide as claimed in claim 8 in an amount sufficient to inhibit sPLA$_2$ mediated release of fatty acid and to thereby inhibit or prevent the arachidonic acid cascade and its deleterious products.

21. A 1H-indole-1-functional compound or a pharmaceutically acceptable salt thereof; wherein said compound is selected from the group represented by the formulae:

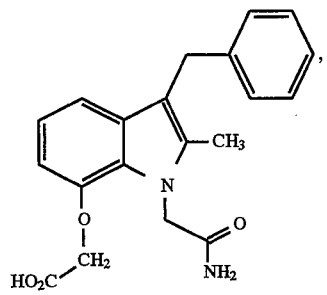

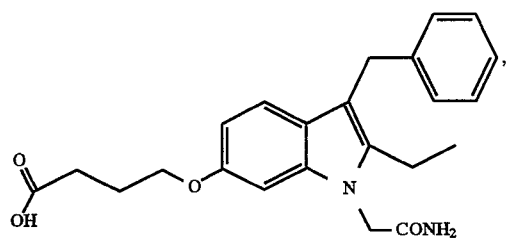

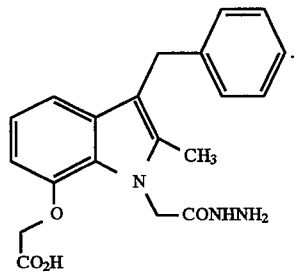

* * * * *